United States Patent
Wells et al.

(10) Patent No.: US 8,873,061 B1
(45) Date of Patent: Oct. 28, 2014

(54) SYSTEMS AND METHODS FOR MEASURING A PHYSICAL PARAMETER OF A SUBSTANCE BASED ON AN ISOCLINIC POINT IN THE ABSORPTION SPECTRUM OF ANOTHER SUBSTANCE

(71) Applicant: The Aerospace Corporation, El Segundo, CA (US)

(72) Inventors: Nathan P. Wells, Marina Del Rey, CA (US); James C. Camparo, Redondo Beach, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 14/019,235

(22) Filed: Sep. 5, 2013

(51) Int. Cl.
  *G01N 21/00* (2006.01)
  *H01S 3/13* (2006.01)
  *G01K 11/00* (2006.01)
  *G01N 21/39* (2006.01)

(52) U.S. Cl.
  CPC ............... *G01N 21/39* (2013.01); *G01K 11/00* (2013.01)
  USPC ........................................................ 356/437

(58) Field of Classification Search
  CPC ............................... H01S 3/13; H01S 3/1392
  USPC ....................................................... 356/437
  See application file for complete search history.

(56) References Cited

U.S. PATENT DOCUMENTS

| | | | |
|---|---|---|---|
| 4,833,681 A | 5/1989 | Akiyama et al. | |
| 5,392,303 A | 2/1995 | Shiozawa et al. | |
| 5,553,087 A | 9/1996 | Telle | |
| 6,151,340 A | 11/2000 | Rivers | |
| 8,050,301 B2 * | 11/2011 | Wells et al. | 372/32 |
| 8,442,083 B2 * | 5/2013 | Wells et al. | 372/32 |

OTHER PUBLICATIONS

About Lock-In Amplifiers, Application Note #3. SRS Application Notes [online]. Standford Research Systems, Inc. Retrieved from the Internet: <URL:www.thinksrs.com/downloads/PDFs/Application-Notes/AboutLIAs.pdf> , (retrieved on Sep. 4, 2013).

Affolderbach et al., "A compact laser head with high-frequency stability for Rb atomic clocks and optical instrumentation," Review of Scientific Instruments 76, 073108. 5 pages (2005).

Calosso et al., "Enhanced temperature sensitivity in vapor-cell frequency standards," IEEE Transactions on Utrasonics, Ferroelctrics, and Frequency Control, 59(12):2646-2654 (2012).

(Continued)

*Primary Examiner* — Roy M Punnoose
(74) *Attorney, Agent, or Firm* — Jones Day; Jaime D. Choi

(57) ABSTRACT

Systems and methods measure a physical parameter of a first substance having an absorption feature that varies based on the physical parameter. A tunable-frequency laser may transmit a first laser beam through the first substance and a second laser beam through a second substance having an isoclinic point. A first output is based on an intensity of the first laser beam transmitted through the first substance, and a second output is based on an intensity of the second laser beam transmitted through the second substance. Controller circuitry locks a first frequency of the first laser beam to the absorption feature based on the first output, and locks a second frequency of the second laser beam to the isoclinic point based on the second output. Measurement circuitry calculates the physical parameter of the first substance based on a difference between the first and second frequencies.

34 Claims, 9 Drawing Sheets

(56) References Cited

OTHER PUBLICATIONS

Camparo, "The rubidium atomic clock and basic research," Physics Today, 11:33-39 (2007).

Furuta et al., "Evaluations of frequency shift and stability in rubidium vapor stabilized semiconductor lasers," Applied Optics 28(17), 3737-3743 (Sep. 1, 1989).

International Union of Pure and Applied Chemistry (IUPAC), "Glossary of terms used in photochemistry," Pure & Appl. Chem. 68(12), 4 pages (1996).

Knappe, et al., "A microfabricated atomic clock," Applied Physics Letters, 85(9):1460-1462 (2004).

Schawlow, "Spectroscopy in a new light," Reviews of Modern Physics 54(3), 13 pages (Jul. 1982).

Tetu et al., "Toward the realization of a wavelength standard at 780 nm based on a laser diode frequency locked to rubidium vapor," IEEE Transactions on Instrumentation and Measurement 40(2), 191-195 (Apr. 1991).

Weel et al., "Laser-frequency stabilization using a lock-in amplifier," Can. J. Phys. 80, 1449-1458 (2002).

Wells et al., "87Rb D1 isoclinic point," Physical Review A 82, 062505 (2010).

Whiting, "An empirical approximation to the Voigt profile," J. Quant. Spectrosc. Radiat. Transfer 8, 1379-1384 (1968).

* cited by examiner

SYSTEMS AND METHODS FOR MEASURING A PHYSICAL PARAMETER OF A SUBSTANCE BASED ON AN ISOCLINIC POINT IN THE ABSORPTION SPECTRUM OF ANOTHER SUBSTANCE

FIELD

This application generally relates to systems and methods for measuring a physical parameter based on a feature in the absorption spectrum of a substance.

RELATED ART

Certain types of devices or experiments rely upon precise knowledge or control of the temperature of a substance. For example, as is known in the art, atomic clocks may lock a laser frequency to a feature in the absorption spectrum of a gas, such as an alkali gas, and may generate a signal based on the locked laser frequency based upon which location may be determined. However, if the temperature or other physical parameter of the gas changes, such as the pressure, density, phase, or exposure to an electric or magnetic field, the absorption feature to which the laser frequency is locked may change, thus generating an error in the signal and thus an error in the determined location.

For example, current gas-cell atomic clocks, as well as gas-cell based magnetometers, use a contact-type temperature sensor for thermal control. Briefly, in the simplified system 10 illustrated in FIG. 1, laser 11 passes a laser beam having frequency $\omega_L$ through gas cell 12 that contains a gas, and photodetector 13 generates an output signal based on the intensity of the laser beam transmitted through gas cell 12. The output signal of photodetector 13 is provided to controller circuitry 14, which in turn may communicate with laser 11 so as to tune the wavelength of the laser beam to a selected feature in the absorption spectrum of the gas within gas cell 12. System 10 further may include thermocouple or thermistor 15, which may be bonded to one or more points of the outer surface of gas cell 12. Temperature variations in gas cell 12 are sensed by thermocouple or thermistor 15 and provided to controller circuitry 14, which in turn may adjust the output of heater 16 so as to maintain the temperature measured by the thermocouple at a desired value, using a feedback loop.

More specifically, the gas within gas cell 12 preferably has an absorption spectrum characterized by one or more peaks corresponding to atomic or molecular transitions. As the light from laser 11 transmits through cell 12, the light may interact with one or more transitions of the gas within cell 12. Specifically, if the frequency $\omega_L$ of the laser light is resonant, or near-resonant, with a transition of the gas at frequency $\omega_A$, then that transition (which appears as a peak in the absorption spectrum of the gas) will at least partially absorb the laser light. Such an absorption reduces the intensity of laser light transmitted through gas cell 12. Thus, the closer the laser frequency $\omega_L$ is to the absorption peak $\omega_A$ of the gas, the lower the transmitted intensity. Photodetector 13 measures the intensity of the transmitted light and generates an output that is provided to controller circuitry 14. Based on the output of photodetector 13, controller circuitry 14 determines whether laser frequency $\omega_L$ is on-resonance with the transition (i.e., $\omega_L$ is at the peak $\omega_A$ of the absorption line for that transition), and if not, the circuitry may adjust the driver current of laser 11 so as to bring $\omega_L$ closer to resonance. Photodetector 13 then measures the intensity of the new frequency $\omega_L$ of laser light transmitted through cell 12, and the output is provided to circuitry 14, which may send further signals to laser 11 to bring $\omega_L$ still closer to resonance, if required. In other words, a feedback loop may be used to lock laser 11 to a peak in the absorption spectrum of the gas within cell 12.

Specifically, the frequency difference between the laser frequency $\omega_L$ and the frequency absorption peak $\omega_A$ may be modulated, which causes modulation in the intensity measured by photodetector 13. The output of the photodetector 13 provides a dispersive-shaped error signal: positive voltage when $\omega_L > \omega_A$, negative voltage when $\omega_L < \omega_A$, and zero voltage when $\omega_L = \omega_A$. The error signal is employed in a feedback loop to lock the laser frequency to a particular value, typically the frequency where the error signal is zero: $\omega_L = \omega_A$. The shape of the error signal is proportional to the derivative of the absorption spectrum, so that any changes in physical parameter(s) that cause a change in the absorption frequency $\omega_A$ will produce frequency shifts in the laser lock frequency $\omega_L$, as described in greater detail below.

As is familiar to those of ordinary skill in the art, controller circuitry 14 may include a lock-in amplifier that generates a sinusoidal signal, and a current controller that controls the driver current of laser 11. The lock-in amplifier provides the sinusoidal signal to the current controller, causing the current controller to sinusoidally vary the driver current of laser 11 about a central current selected to generate frequency $\omega_L$. This sinusoidal current variation causes the laser frequency to vary sinusoidally about frequency $\omega_L$, typically by a relatively small amount. The sinusoidal variation about frequency $\omega_L$ causes the intensity of light transmitted through cell 12 to similarly vary sinusoidally, as the variation periodically brings the frequency closer or further from the absorption peak $\omega_A$. Photodetector 13 records the sinusoidal variations in the intensity of transmitted light, and the photodetector output is provided to the lock-in amplifier. The lock-in amplifier carries on-board circuitry that locks to the sinusoidally varying output signal. The current controller may then vary the central current so as to bring the central frequency $\omega_L$ closer to the absorption peak $\omega_A$, which will be detected as a decreased signal at the photodetector 13. For further details, see the following references, the entire contents of each of which are incorporated by reference herein: Weel et al., Can. J. Phys. 80, 1449-1458 (2002); Furuta et al., Appl. Opt. 28(17), 3737-3743 (1989); Akiyama et al., U.S. Pat. No. 4,833,681; Telle, U.S. Pat. No. 5,553,087; and Têtu et al., IEEE Trans. Instrum. Meas. 40(2), 191-195 (1991).

In one example, the gas within cell 12 is hydrogen cyanide ($H^{13}C^{14}N$), the absorption spectrum of which has a series of several spaced peaks between about 1525-1565 nm that correspond to rotational-vibrational transitions, also referred to as ro-vibrational transitions. Laser 11 may be locked to any one of these peaks. In another example, the gas within cell 12 is rubidium-87 ($^{87}Rb$), which may be successfully employed with a significantly lower vapor pressure (e.g., $2 \times 10^{-6}$ torr) than hydrogen cyanide (e.g., about 10 torr), resulting in essentially collisionless conditions. As known to those of ordinary skill in the art, $^{87}Rb$ has four $D_1$ electronic transitions 20 illustrated in FIG. 2A, corresponding to peaks A, B, C, and D in the atomic absorption spectrum 21 of $^{87}Rb$ at 35° C., illustrated in FIG. 2B. Specifically, $^{87}Rb$ has four hyperfine electronic transitions: $5^2S_{1/2}$ ($F_g=2$) to $5^2P_{1/2}$ ($F_e=1$), corresponding to peak A; $5^2S_{1/2}$ ($F_g=2$) to $5^2P_{1/2}$ ($F_e=2$), corresponding to peak B; $5^2S_{1/2}$ ($F_g=1$) to $5^2P_{1/2}$ ($F_e=1$), corresponding to peak C; and $5^2S_{1/2}$ ($F_g=1$) to $5^2P_{1/2}$ ($F_e=2$), corresponding to peak D. Note that although each of the transitions is characterized by a single frequency, the corresponding peak in the absorption spectrum is somewhat broadened because of Doppler broadening, leading to overlap between the peaks. The x-axis of FIG. 2B, "laser detuning,"

refers to the frequency by which laser 11 may be detuned from the "center of gravity" of the optical spectrum (3.77× $10^{14}$ Hz) to match the absorption feature in the drawing.

As illustrated in FIG. 2B, the laser is typically locked to frequency 23, which corresponds to the $5^2S_{1/2}$ ($F_g$=1) to $5^2P_{1/2}$ ($F_e$=2) electronic transition (the maximum of peak D). This frequency is typically selected because of the four illustrated absorption peaks A-D, peak D overlaps the least with an adjacent peak (peak C). However, as is familiar to those of ordinary skill in the art, the presence of overlapping peaks in the absorption spectrum "pulls" the laser frequency $\omega_L$ away from the true center of the desired peak. The breadth of each of peaks A-D may vary as a function of the gas temperature, due to Doppler broadening, and the relative amplitude of the peaks may also vary as a function of the gas temperature, because of the nonlinear nature of resonant absorption, e.g., because of Beer-Lambert exponential attenuation. As the breadths and/or heights of the different peaks change, the amount of overlap—and thus the amount of pulling—may also increase or decrease with temperature, and as a consequence the peaks of the absorption lines may shift with the vapor's temperature. Note that according to the Beer-Lambert law, the transmitted intensity I is equal to $I_o e^{-N\sigma L}$, where N is the number density of atoms or molecules in the gas, $\sigma$ is the absorption cross-section, and L is the gas length. The shape of the absorption spectrum (e.g., I versus the laser frequency $\omega$) will mimic the shape of the absorption cross section $\sigma$ for optically thin gases, where $N\sigma L \ll 1$. For optimized laser stabilization systems, where $N\sigma L \sim 1$, the detailed shape of the absorption spectrum may deviate from the absorption cross section $\sigma$, and will depend on N. Specifically, the absorption spectrum will have a width that increases with N.

One way of reducing the change in the locking frequency is sub-Doppler spectroscopy. In such a technique, the apparent Doppler broadening is reduced by irradiating gas cell 12 with overlapping, counter-propagating laser beams. Each of the counter-propagating beams experiences an opposite Doppler shift as the other, canceling out the Doppler broadening effect. For further details, see Schawlow, Rev. Mod. Phys. 54(3), 697-707 (1982), the entire contents of which are incorporated by reference herein. However, sub-Doppler spectroscopy may not be available to eliminate all sources of pulling, such as pressure broadening.

Another way of reducing the change in the locking frequency is to control the temperature of gas cell 12 using a feedback look in which controller circuitry 14 monitors the temperature of gas cell 12 as measured by thermocouple or thermistor 15, and provides an appropriate control signal to heater 16 so as to maintain the temperature of the gas cell at a desired value. However, multiple issues arise with the use of a temperature sensor that is attached to the outside of a gas cell, e.g., thermocouple or thermistor 15 attached to gas cell 12 illustrated in FIG. 1. First, the temperature measured by such a temperature sensor corresponds to the temperature of the outside of the gas cell, rather than the temperature of the gas itself. For certain applications, the temperature of the outside of the gas cell suitably may be used as an approximation of the temperature of the gas itself. However, for precise timekeeping, fractional frequency temperature sensitivities $(\delta f/f_o)/\delta T$ may be on the order of $10^{-1}/°$ C. to $10^{-11}/°$ C., where $f_o$ is the nominal laser frequency, $\delta f$ is the change in laser frequency and T is temperature. Accordingly, small discrepancies between the sensed temperature of the gas cell and the actual temperature of the gas therein may yield measurable and significant degradations of clock frequency stability. Additionally, contact-type measurements may record the temperature at only a point, or at a few points. If there is a temperature gradient across gas cell 12, and the temperature gradient changes, then the point of contact between the thermocouple or thermistor may become a better or poorer approximation for the actual temperature of the gas.

For example, in global positioning system (GPS) atomic clocks based on rubidium (Rb), the temperature sensitivity of the clock's gas cell is approximately $(\delta f/f_o)/\delta T=3\times 10^{-11}/°$ C., based upon which a temperature error of $\pm 0.01°$ C. may lead to a GPS positioning error of about 26 feet. Accordingly, the temperature of rubidium gas cells in GPS clocks preferably does not vary by more than about $10^{-3}°$ C. over the span of several hours. Although such temperature control is presently attempted using a feedback loop such as illustrated in FIG. 1, the GPS atomic clocks typically must be remotely synchronized on a daily basis so as to limit the effects any temperature-based drifts that may occur.

Thus, what is needed is an improved way to measure a physical parameter, such as the temperature, of a substance.

SUMMARY

Embodiments of the invention provide systems and methods for measuring a physical parameter of a substance based on an isoclinic point in the absorption spectrum of another substance. An isoclinic point is defined to be "[a] wavelength, wavenumber, or frequency at which the first derivative of an absorption spectrum of a sample does not change upon a chemical reaction or physical change of the sample." For many of the systems and methods disclosed herein, the isoclinic point is a point in the absorption spectrum of a gas that falls in between two overlapping absorption peaks of substantially equal amplitude, and which experience substantially the same broadening as a function of a physical parameter, e.g., as a function of temperature or pressure. Because the two peaks have substantially equal amplitude as one another, the isoclinic point is a saddle point (local minimum) in the region of overlap between the two peaks. As the peaks are evenly broadened due to a change in the physical parameter, the frequency of the isoclinic point does not significantly change, but instead remains at substantially constant frequency, independent of the physical parameter. As such, the isoclinic point suitably may be used as a reference by which a physical parameter of another substance may be measured.

Under one aspect of the present invention, a system is provided for measuring a physical parameter of a first substance having a first absorption spectrum with an absorption feature that varies based on the physical parameter. The system may include a second substance having a second absorption spectrum including first and second peaks respectively corresponding to first and second transitions of the second substance. The first and second peaks preferably overlap with one another, a point in the overlap between the first and second peaks defining an isoclinic point of the absorption spectrum of the second substance. The system further may include at least one tunable-frequency laser configured to transmit a first laser beam through the first substance and to transmit a second laser beam through the second substance. A first photodetector may be configured to generate a first output based on an intensity of the first laser beam transmitted through the first substance, and a second photodetector may be configured to generate a second output based on an intensity of the second laser beam transmitted through the second substance. The system further may include controller circuitry configured to tune the at least one tunable-frequency laser so as to lock a first frequency of the first laser beam to the absorption feature of the first substance based on the first output, and to tune the at least one tunable-frequency laser so as to lock a second frequency of the second laser beam to the isoclinic point of the second substance based on the second output. The system further may include measurement circuitry configured to calculate the physical parameter of the first substance based on a difference between the first and second frequencies.

In some embodiments, the at least one tunable-frequency laser comprises a first tunable-frequency laser configured to generate the first laser beam and a second tunable-frequency laser configured to generate the second laser beam. The controller circuitry may include a first lock-in amplifier configured to receive the first output and to generate a first error signal based on the first output, and a first controller in operable communication with the first tunable-frequency laser and the first lock-in amplifier. The first controller may be configured to tune the first frequency of the first tunable-frequency laser so as to minimize the first error signal and thus lock the first frequency to the temperature-dependent absorption feature of the first substance. The controller circuitry further may include a second lock-in amplifier configured to receive the second output and to generate a second error signal based on the second output, and a second controller in operable communication with the second tunable-frequency laser and the second lock-in amplifier. The second controller may be configured to tune the second frequency of the second tunable-frequency laser so as to minimize the second error signal and thus lock the second frequency to the isoclinic point of the second substance.

Some embodiments further include an optical component configured to generate an optical heterodyne of the first and second laser beams, the optical heterodyne having a beat frequency based on the difference between the first and second frequencies. The measurement circuitry may include a third photodetector configured to generate a third output based on the optical heterodyne, a frequency counter configured to determine the beat frequency based on the third output, and a calculation module configured to calculate the physical parameter based on the determined beat frequency and a calibration constant. In some embodiments, the optical component includes a beamsplitter configured to receive a portion of each of the first and second laser beams and to direct the received portions to the third photodetector.

The first and second controllers may be respectively configured to tune the first and second tunable-frequency lasers by respectively adjusting driver currents of the first and second tunable-frequency lasers.

In other embodiments, the at least one tunable-frequency laser is configured to generate a frequency comb comprising the first frequency and the second frequency, the first and second frequencies being separated from one another by an integer multiple of a spacing of the frequency comb. The controller circuitry may include a first lock-in amplifier configured to receive the first output and to generate a first error signal based on the first output, and a first controller in operable communication with the at least one tunable-frequency laser and the first lock-in amplifier. The first controller may be configured to tune the first frequency of the at least one tunable-frequency laser so as to minimize the first error signal and thus lock the first frequency to the temperature-dependent absorption feature of the first substance. The controller circuitry further may include a second lock-in amplifier configured to receive the second output and to generate a second error signal based on the second output, and a second controller in operable communication with the at least one tunable-frequency laser and the second lock-in amplifier. The second controller may be configured to tune the spacing of the at least one tunable-frequency laser so as to minimize the second error signal and thus lock the second frequency to the isoclinic point of the second substance.

Alternatively, the controller circuitry may include a first lock-in amplifier configured to receive the first output and to generate a first error signal based on the first output, and a first controller in operable communication with the at least one tunable-frequency laser and the first lock-in amplifier. The first controller may be configured to tune the spacing of the at least one tunable-frequency laser so as to minimize the first error signal and thus lock the first frequency to the temperature-dependent absorption feature of the first substance. The controller circuitry further may include a second lock-in amplifier configured to receive the second output and to generate a second error signal based on the second output, and a second controller in operable communication with the at least one tunable-frequency laser and the second lock-in amplifier. The second controller may be configured to tune the second frequency of the at least one tunable-frequency laser so as to minimize the second error signal and thus lock the second frequency to the isoclinic point of the second substance.

In some embodiments, the measurement circuitry is configured to determine the spacing of the at least one tunable-frequency laser based on a third output of the at least one tunable-frequency laser, to determine the difference between the first and second frequencies based on the determined spacing, and to calculate the physical parameter based on the determined difference and a calibration constant.

In some embodiments, the second substance includes an atomic gas, and the first and second transitions are electronic transitions of atoms in the atomic gas. The atomic gas may include, for example, an alkali selected from the group consisting of $^{87}$Rb, $^{7}$Li, $^{23}$Na, $^{39}$K, and $^{41}$K. In some embodiments, the first substance includes the atomic gas, and the absorption feature corresponds to a third electronic transition of the atomic gas. The first substance may further include a buffer gas.

In some embodiments, the absorption feature of the first substance corresponds to an atomic electronic transition, a molecular electronic transition, a vibrational transition, a rotational transition, or a rovibrational transition.

The physical parameter may include temperature, pressure, density, phase, or exposure to an electric or magnetic field.

The system may further include adjustment circuitry configured to adjust the physical parameter of the first substance based on the determined physical parameter.

Under another aspect of the present invention, a method is provided for measuring a physical parameter of a first substance having a first absorption spectrum with an absorption feature that varies based on the physical parameter. The method may include transmitting a first laser beam through the first substance, and transmitting a second laser beam through a second substance having a second absorption spectrum including first and second peaks respectively corresponding to first and second transitions of the second substance. The first and second peaks may overlap with one another, a point in the overlap between the first and second peaks defining an isoclinic point of the absorption spectrum of the second gas. The method also may include generating a first output based on an intensity of the first laser beam transmitted through the first substance, and generating a second output based on an intensity of the second laser beam transmitted through the second substance. The method also may include locking a first frequency of the first laser beam to the absorption feature of the first substance based on the first output, and locking a second frequency of the second laser beam to the isoclinic point of the second substance based on the second output. The method also may include calculating the physical parameter of the first substance based on a difference between the first and second frequencies.

DETAILED DESCRIPTION

Overview

Embodiments of the present invention provide systems and methods for measuring a physical parameter of a substance based on an isoclinic point in the absorption spectrum of another substance. As noted above, prior art methods for measuring the temperature of a gas typically have been based on placing contact-type sensors such as thermocouples or thermistors on the outside of the cell containing the gas. However, the present inventors have recognized that the temperature on the outside of the gas cell may not necessarily be the same as the temperature of the gas, and that therefore an improved method for directly measuring the temperature—or other physical parameter—of the gas is needed. In particular, the present inventors have recognized that the isoclinic point of a first substance suitably may be used to measure a physical parameter of a second substance.

As described in greater detail below, the isoclinic point in the absorption spectra of certain substances is believed to be substantially stable over a useful range of physical parameters, and thus suitably may be used to measure the physical characteristic of another substance. More specifically, a first substance may have an absorption spectrum that includes an absorption feature that varies based on a physical parameter, such as temperature, pressure, density, phase, or exposure to an electric or magnetic field, while a second substance may have an absorption spectrum that includes an isoclinic point. A first laser beam may be transmitted through the first substance and frequency-locked to the absorption feature, while a second laser beam may be transmitted through the second substance and frequency-locked to the isoclinic point, and a physical parameter of the first substance may be measured based on a difference in the locked frequencies of the first and second laser beams may be determined. More specifically, a change in physical characteristic of the first substance may cause a change in the absorption feature of that substance, and thus may cause a change in the locked frequency of the first laser beam; however, a similar change in physical characteristic of the second substance may not cause a change in the isoclinic point of that substance, and thus may not cause a change in the locked frequency of the second laser beam. By measuring the difference between the frequencies locked to the first and second substances, the physical characteristic of the first substance may be determined.

First, some illustrative embodiments of systems and methods for measuring a physical parameter of a substance based on an isoclinic point in the absorption spectrum of another substance, and alternative embodiments, will be described. Then, an overview of isoclinic points will be provided. Lastly, experimental results will be described.

Figure 3A:
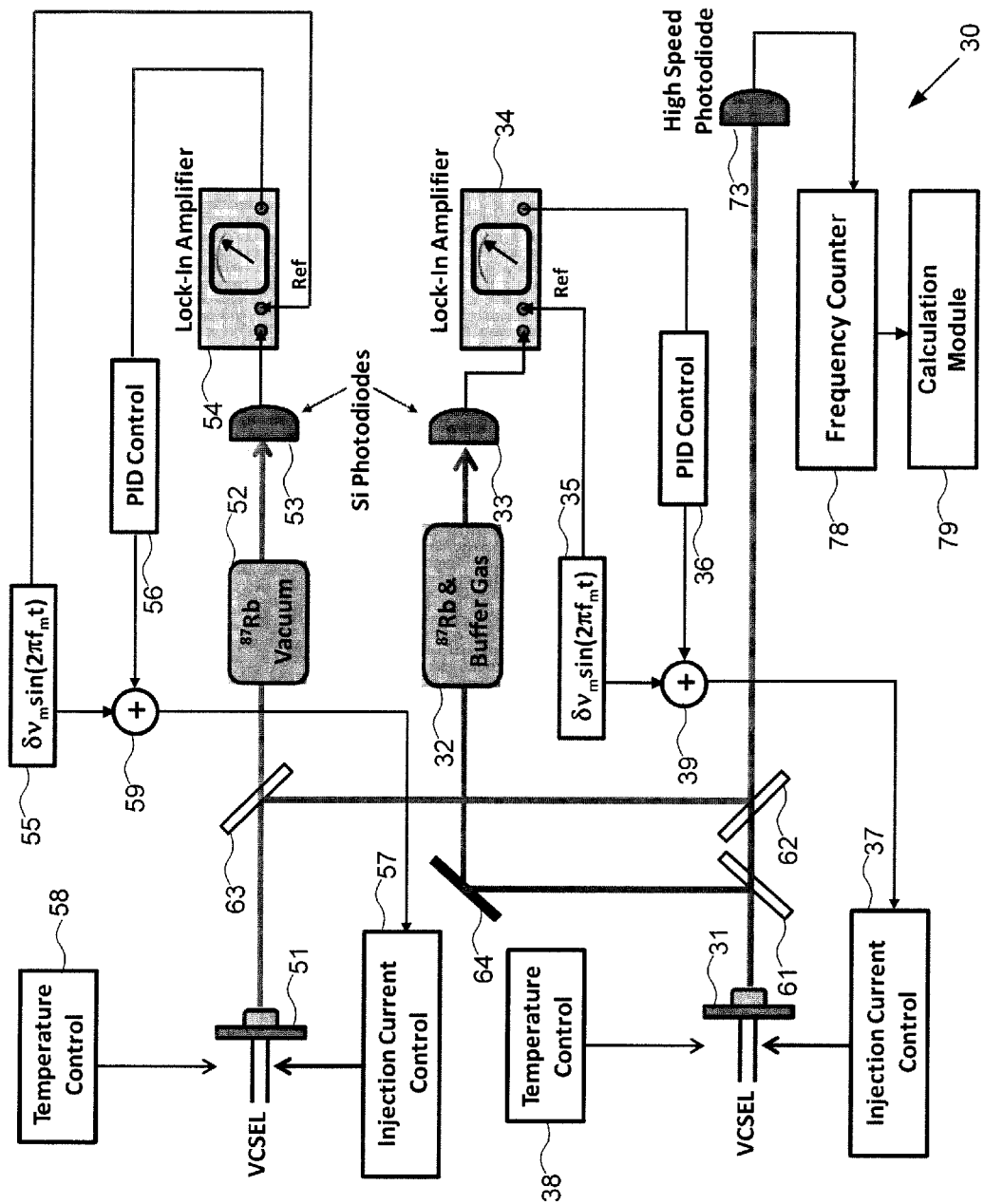
FIG. 3A schematically illustrates an exemplary system for measuring a physical characteristic of a substance based on an isoclinic point in the absorption spectrum of another substance, according to some embodiments of the present invention.

Exemplary Systems and Methods for Measuring Physical Characteristic of a Substance Based on an Isoclinic Point in the Absorption Spectrum of Another Substance FIG. 3A illustrates a first exemplary system 30 for measuring a physical characteristic of a first substance based on an isoclinic point in the absorption spectrum of another substance, according to some embodiments of the present invention.

System 30 includes first laser 31, second laser 51, first transmission cell 32 containing a first substance, second transmission cell 52 containing a second substance, first photodetector 33, second photodetector 53, beamsplitters 61, 62, and 63, mirror 64; controller circuitry that includes first lock-in amplifier 34, second lock-in amplifier 54, first frequency modulator 35, second frequency modulator 55, first proportional-integral-derivative (PID) controller 36, second PID controller 56, first injection current controller 37, second injection current controller 57, first laser temperature controller 38, second laser temperature controller 58, first addition module 39, second addition module 59; and measurement circuitry that includes third photodetector 73, frequency counter 78, and calculation module 79.

First laser 31 may be any suitable laser, including a continuous-wave (CW) or pulsed laser, the frequency of which is tunable via any suitable mechanism. In one illustrative embodiment, first laser 31 is a diode laser, e.g., a vertical-cavity surface emitting laser (VCSEL), the frequency of which is tunable by adjusting the driver current applied to the diode via first injection current controller 37 while holding the temperature of the diode constant using first laser temperature controller 38, as described in greater detail below. Alternatively, the frequency of first laser 31 may be tuned using any suitable combination of driver current via first injection current controller 37 and temperature via first laser temperature controller 38.

As illustrated in FIG. 3A, first laser 31 is configured to transmit a laser beam through first transmission cell 32. For example, beamsplitter 61 may be configured to reflect a portion of the laser beam from first laser 31 towards mirror 64, which directs the beam through first transmission cell 32 and then onto first photodetector 33. Beamsplitter 61 transmits the remaining portion of the laser beam towards and through beamsplitter 62, which combines the beam with a portion of the laser beam from second laser 51 at third photodetector 73, so as to generate an optical heterodyne between the laser beans from the first and second lasers 31, 51 and thus to obtain a beat frequency representative of the physical parameter of the substance within first transmission cell 32, as described in greater detail below. It should be appreciated that other optical arrangements suitably may be used.

First transmission cell 32 contains a first substance that has an absorption spectrum with an absorption feature that varies based on a physical parameter. For example, as is known in the art, various substances may have transitions with absorption peaks that vary as a function of temperature, pressure, density, phase, or exposure to an electric or magnetic field. In the illustrated embodiment, the substance contained within first transmission cell 32 is a mixture of an alkali gas such as $^{87}$Rb and a buffer gas such as nitrogen, argon, or a mixture thereof, such as may be used in an atomic clock or alkali magnetometer. Features in the absorption spectrum of such a mixture may be shifted relative to corresponding features in a gas of pure $^{87}$Rb as a consequence of what is sometimes referred to as a "pressure shift." Specifically, collisions between atoms or molecules of the buffer gas and the alkali may perturb the energy level structure of the alkali, and thereby shift the resonant frequencies of the alkali's absorption lines. Although this collision-based shift is proportional to the density of buffer gas atoms or molecules, the shift historically has been referred to as a "pressure shift." For example, in a sealed glass vapor cell with a constant density of buffer gas, a change in temperature will alter the pressure as a consequence of the ideal gas law. However, this simple pressure increase may not alter the magnitude of the "pressure shift," because the number density of buffer gas atoms or molecules remains unchanged. Preferably, regardless of the particular physical mechanism, an absorption feature in the absorption spectrum of the first substance within first transmission cell 32 varies based on changes in a physical parameter of interest. For example, for a mixture of $^{87}$Rb and buffer gas illustrated in FIG. 3A at a pressure of about $10^{-4}$ torr of $^{87}$Rb and a pressure of a few tens of torr of a buffer gas having a mixture of nitrogen and argon, the "pressure shift" of absorption features in the $^{87}$Rb scales with temperature $T^{\alpha}$, where T is temperature and a typically has a value between about 0.3 and 0.5.

Figure 1:
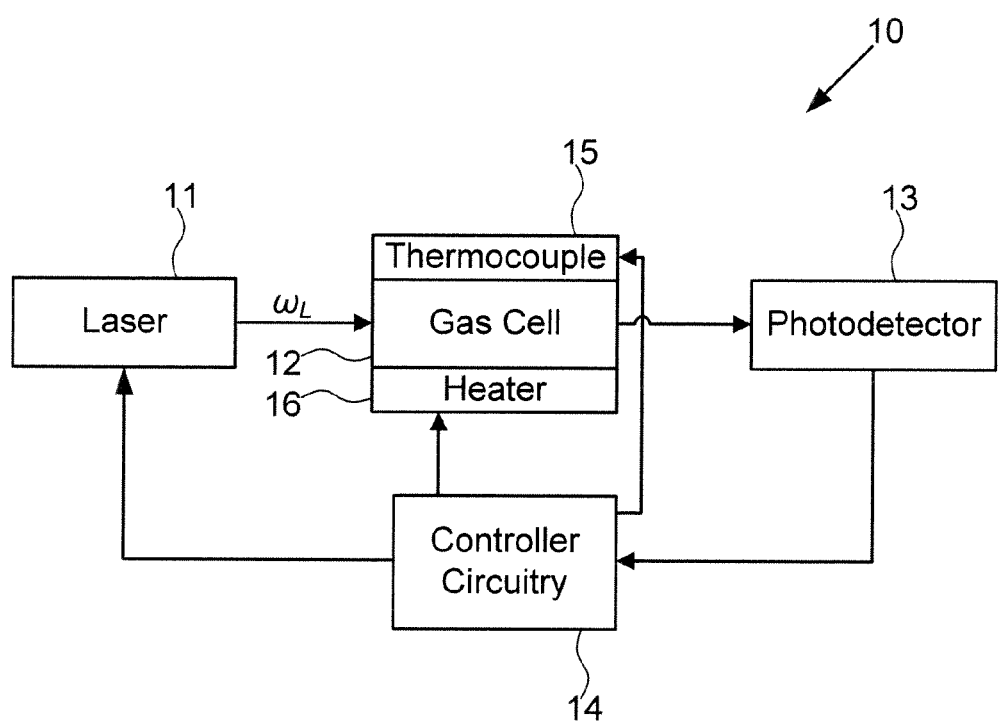
FIG. 1 schematically illustrates a prior art system for measuring and controlling the temperature of a gas cell, such as used in an atomic clock.

First photodetector 33, which in the illustrated embodiment is a silicon (Si) based photodiode, is configured to generate a first output based on an intensity of the beam from first laser 31 transmitted through first transmission cell 32. The intensity of the beam from first laser 31 transmitted through first transmission cell and received by first photodetector 33, and thus the magnitude of the first output, depends on the frequency of the laser beam relative to absorption features in the absorption spectrum of the substance within first transmission cell 32, in a manner analogous to that described above with reference to FIG. 1.

First photodetector 33 is configured to provide the first output to lock-in amplifier 34, which also is coupled to receive input from first frequency modulator 35 and to provide an output to first PID controller 36. First frequency modulator 35 and first PID controller 36 are both configured to provide outputs to first addition module 39, which in turn is configured to output a control signal to first injection current controller 37. More specifically, first frequency modulator 35 is configured to transmit both to lock-in amplifier 34 and to addition module 39 a sinusoidally varying signal of value $\delta v_m \sin(2\pi f_m t)$, where $\delta v_m$ is the magnitude of the signal, $f_m$, is the frequency of the signal, and t is time. Lock-in amplifier 34 is configured to calculate and to output to PID controller 36 an error signal based on the first output from photodetector 33 and the sinusoidally varying signal from first frequency modulator 35. First PID controller is configured to calculate and to transmit to addition module 39 an adjustment signal selected to reduce the error signal from lock-in amplifier 34 using known feedback loop algorithms. Addition module 39 generates and transmits to injection current controller 37 a control signal based on the adjustment signal and the sinusoidally varying signal from first frequency modulator 35 that brings the frequency of the laser beam from first laser 31 closer to—and eventually to lock on to—an absorption feature of the substance within first transmission cell 32, using known feedback loop algorithms and techniques.

Second laser 51 may be any suitable laser, including a continuous-wave (CW) or pulsed laser, the frequency of which is tunable via any suitable mechanism. In one illustrative embodiment, second laser 51 is a diode laser, e.g., a vertical-cavity surface emitting laser (VCSEL), the frequency of which is tunable by adjusting the driver current applied to the diode via second injection current controller 57 while holding the temperature of the diode constant using second laser temperature controller 58, as described in greater detail below. Alternatively, the frequency of second laser 51 may be tuned using any suitable combination of driver current via second injection current controller 57 and temperature via second laser temperature controller 58.

As illustrated in FIG. 3A, second laser 51 is configured to transmit a laser beam through second transmission cell 52. For example, beamsplitter 63 may be configured to transmit a portion of the laser beam from second laser 51 through second transmission cell 52 and then onto second photodetector 53. Beamsplitter 63 reflects the remaining portion of the laser beam towards beamsplitter 62, which combines the beam with a portion of the laser beam from first laser 31 at third photodetector 73, so as to generate an optical heterodyne between the laser beans from the first and second lasers 31, 51 and thus to obtain a beat frequency representative of the physical parameter of the substance within first transmission cell 32, as described in greater detail below. It should be appreciated that other optical arrangements suitably may be used.

Second transmission cell 52 contains a second substance that has an absorption spectrum with an isoclinic point, e.g., has first and second peaks respectively corresponding to first and second transitions of the second substance, the first and second peaks overlapping with one another, a point in the overlap between the first and second peaks defining an isoclinic point in the absorption spectrum of the second substance. In the illustrated embodiment, the substance contained within second transmission cell 52 is an alkali gas such as $^{87}$Rb "in vacuum," meaning that substantially no other gases besides $^{87}$Rb are present. Preferably, the isoclinic point in the absorption spectrum of the second substance within second transmission cell 52 substantially does not vary based on changes in physical parameters of that substance. For an overview of isoclinic points, see further below, and for greater detail see U.S. Pat. Nos. 8,050,301 and 8,442,083 to Wells et al., the entire contents of both of which are incorporated by reference herein. In one example, the pressure of $^{87}$Rb within second transmission cell 52 is about $10^{-4}$ torr. Although such a pressure is approximately equivalent to the pressure of $^{87}$Rb in first transmission cell 32, the absorption spectrum of the $^{87}$Rb in the first transmission cell, which also contains a buffer gas, is expected to have significantly shifted absorption peaks as compared to the $^{87}$Rb in the second transmission cell 52, where the shift is proportional to the relative pressure shift between the first and second transmission cells.

Second photodetector 53, which in the illustrated embodiment is a silicon (Si) based photodiode, is configured to generate a second output based on an intensity of the beam from second laser 51 transmitted through second transmission cell 52. Second photodetector 53 is configured to provide the second output to lock-in amplifier 54, which also is coupled to receive input from second frequency modulator 55 and to provide an output to second PID controller 56. Second frequency modulator 55 and second PID controller 56 are both configured to provide outputs to second addition module 59, which in turn is configured to output a control signal to second injection current controller 57. More specifically, second frequency modulator 55 is configured to transmit both to lock-in amplifier 54 and to addition module 59 a sinusoidally varying signal of value $\delta v_m \sin(2\pi f_m t)$, where $\delta v_m$ is the magnitude of the signal, $f_m$ is the frequency of the signal, and t is time. Lock-in amplifier 54 is configured to calculate and to output to PID controller 56 an error signal based on the second output from photodetector 53 and the sinusoidally varying signal from second frequency modulator 55. Second PID controller is configured to calculate and to transmit to addition module 59 an adjustment signal selected to reduce the error signal from lock-in amplifier 54 using known feedback loop algorithms. Addition module 59 generates and transmits to injection current controller 57 a control signal based on the adjustment signal and the sinusoidally varying signal from second frequency modulator 55 that brings the frequency of the laser beam from second laser 51 closer to—and eventually to lock on to—an isoclinic point of the substance within second transmission cell 52, using known feedback loop algorithms and techniques.

Preferably, first laser 31 is tunable through a variety of frequencies that correspond to one or more features of the absorption spectrum of the first substance within first transmission cell 32. It should be noted that because different substances may have absorption features in widely different regions of the spectrum, the particular type of first laser 31 and the type of substance used in first transmission cell 32 may be co-selected to respectively provide an output in the desired frequency range and a respective absorption feature to which a frequency of first laser 31 may be locked using first lock-in amplifier 34, first frequency modulator 35, first PID controller 36, first addition module 39, and first injection current controller 37. Analogously, second laser 51 preferably is tunable through a variety of frequencies that correspond to one or more features of the absorption spectrum of the second substance within second transmission cell 52, including an isoclinic point of the second substance. It should be noted that because different substances may have absorption features in widely different regions of the spectrum, the particular type of second laser 51 and the type of substance used in second transmission cell 52 may be co-selected to respectively provide an output in the desired frequency range and an isoclinic point to which a frequency of second laser 51 may be locked using second lock-in amplifier 54, second frequency modulator 55, second PID controller 56, second addition module 59, and second injection current controller 57.

As mentioned above, beamsplitter 62 generates an optical heterodyne between the laser beams from the first and second lasers 31, 51 such that third photodetector 73 receives a beat frequency representative of the difference between the first and second frequencies. When a first frequency of first laser 31 is locked to the absorption feature of the first substance, and a second frequency of second laser 51 is locked to the isoclinic point of the second substance, the physical parameter of the first substance may be calculated based on the beat frequency. More specifically, if changes in the physical parameter of the substance within the first transmission cell 32 cause a change in the first frequency, such changes in the physical parameter also cause a change in the beat frequency from which the change in the physical parameter may be determined.

For example, in the embodiment illustrated in FIG. 3A, photodetector 73 is a high-speed photodiode configured to output to frequency counter 78 a time-resolved signal representative of the beat frequency. Frequency counter 78 is configured to determine a count of the beat frequency, e.g., to determine a numerical representation of the beat frequency, such as "80 MHz," and to output that representation to calculation module 79. Calculation module 79 is configured to calculate the physical parameter of the first substance within first transmission cell 32 based on the numerical representation of the beat frequency. For example, calculation module 79 may store a calibration constant such as "1° C./MHz," "10 Torr/MHz," or "1 Gauss/MHz," and may calculate the physical parameter of the substance within first transmission cell 32 by multiplying the beat frequency by the calibration constant, e.g., to calculate a temperature of 80° C., a pressure of 800 Torr, or a magnetic field of 80 Gauss in the above examples, which are provided purely for illustration and should not be construed as limiting. It should be appreciated that more complex calibration parameters may be used. An illustrative method for determining a calibration constant is described further below in the Examples section. Additionally, other circuitry configured to determine the difference between the first and second frequencies or for calculating a physical parameter based on such a difference suitably may be used.

Note that the beat frequency based upon which calculation module 79 calculates the physical parameter of the first substance is based directly upon the absorption spectrum of that substance. Accordingly, the calculated physical parameter is believed to be significantly more accurate than may be obtained with a thermocouple or thermistor placed in contact with one or more points of the transmission cell containing that substance, as was previously known. For example, the physical parameter of the measured point of the transmission cell may not necessarily be identical to the physical parameter of a substance therein, or there may be a temperature gradient across the transmission cell. In comparison, system 30 obtains a measurement of the physical parameter of the first substance itself, using the isoclinic point of the second substance as a reference point that substantially does not vary based on the physical parameter. Additionally, it is known that a gas is in thermodynamic equilibrium with itself; accordingly, in embodiments in which the first substance is a gas, a measurement of the physical parameter of one portion of the gas, e.g., the portion through which the first laser beam passes, is believed to accurately represent the physical parameter of the entire gas.

Figure 3B:
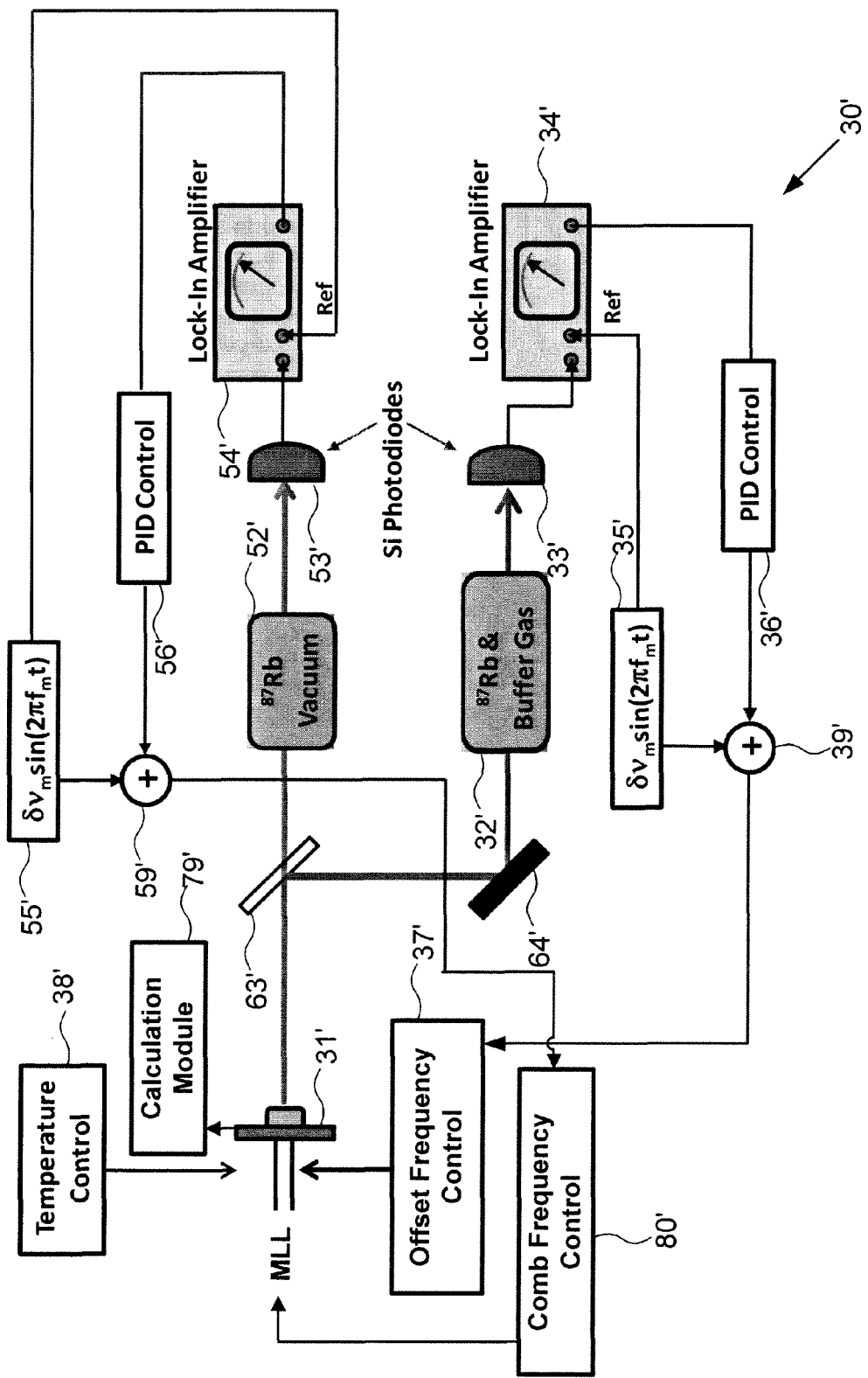
FIG. 3B schematically illustrates an alternative exemplary system for measuring a physical characteristic of a substance based on an isoclinic point in the absorption spectrum of another substance, according to some embodiments of the present invention.

Other arrangements of optical and electronic components suitably may be used to lock a first laser beam to an absorption feature of a first substance that varies based on a physical parameter, to lock a second laser beam to an isoclinic point of a second substance, and to calculate the physical parameter based on a frequency difference between the first and second laser beams. For example, FIG. 3B illustrates an alternative system 30' that is based on the use of a single laser 31' configured to generate a frequency comb, such as a mode-locked laser (MLL), e.g., an ultrafast laser oscillator. As is known in the art, a frequency comb may be generated by outputting a sequence of relatively short optical pulses that are separated in time from one another by the round-trip time of the laser cavity. The frequency spectrum of such a frequency comb includes an offset frequency $\omega_o$ such that $0 \leq \omega_o \leq 1/T_L$, where $T_L$ is the round trip time of the laser, and a plurality of additional frequencies that are spaced relative to one another in frequency space by the inverse of the round trip time of the laser and also may be referred to as the repetition rate of the laser or comb spacing.

System 30' includes laser 31', first transmission cell 32' containing a first substance, second transmission cell 52' containing a second substance, first photodetector 33', second photodetector 53', beamsplitter 63', mirror 64'; controller circuitry that includes first lock-in amplifier 34', second lock-in amplifier 54', first frequency modulator 35', second frequency modulator 55', first PID controller 36', second PID controller 56', injection current controller 37', comb frequency controller 80', laser temperature controller 38', first addition module 39', and second addition module 59'; and measurement circuitry that includes calculation module 79'.

In the embodiment illustrated in FIG. 3B, mode-locked laser (MLL) 31' is configured to generate a frequency comb having first and second frequencies that are separated from one another in frequency by an integer multiple of the comb spacing. The first frequency is directed through first transmission cell 32' containing a first substance having a first absorption spectrum with an absorption feature that varies based on a physical parameter, e.g., a mixture of $^{87}$Rb and a buffer gas, and the second frequency is directed through second transmission cell 52' containing a second substance having a second absorption spectrum with an isoclinic point, e.g., $^{87}$Rb "in vacuum." For example, beamsplitter 63' may be configured to reflect the first frequency from laser 31' towards mirror 64', which directs the beam through first transmission cell 32' and then onto first photodetector 33'. Beamsplitter 63' transmits the second frequency from laser 31' towards and through second transmission cell 52' and then onto second photodetector 53'. It should be appreciated that other optical arrangements suitably may be used.

First photodetector 33', which in the illustrated embodiment is a silicon (Si) based photodiode, is configured to generate a first output based on an intensity of the first frequency from laser 31' transmitted through first transmission cell 32', which in turn depends on the physical parameter of the first substance. First photodetector 33' is configured to provide the first output to first lock-in amplifier 34', which also is coupled to receive input from first frequency modulator 35' and to provide an output to first PID controller 36', which are both configured to provide outputs to first addition module 39', which in turn is configured to output a control signal to offset frequency controller 37' in a manner analogous to that described above for injection current controller 37 with reference to FIG. 3A. First addition module 39' generates and transmits to offset frequency controller 37' a control signal based on the adjustment signal and the sinusoidally varying signal from first frequency modulator 35' that brings the first frequency from first laser 31' closer to—and eventually to lock on to—an absorption feature of the substance within first transmission cell 32', using known feedback loop algorithms and techniques.

As noted above, beamsplitter 63' transmits the second frequency from laser 31' through second transmission cell 52'. For example, beamsplitter 63' may be a dichroic beamsplitter. Second photodetector 53', which in the illustrated embodiment is a silicon (Si) based photodiode, is configured to generate a second output based on an intensity of the second frequency transmitted through second transmission cell 52'. Second photodetector 53' is configured to provide the second output to lock-in amplifier 54', which also is coupled to receive input from second frequency modulator 55' and to provide an output to second PID controller 56', which are both configured to provide outputs to second addition module 59', in a manner analogous to that described above relative to FIG. 3A. However, second addition module 59' is configured to output to comb frequency controller 80' a control signal based on an adjustment signal from lock-in amplifier 54' and a sinusoidally varying signal from second frequency modulator 55' that adjusts the comb spacing so as to bring the second frequency of the laser beam from laser 31' closer to—and eventually to lock on to—an isoclinic point of the second substance within second transmission cell 52', using known feedback loop algorithms and techniques. Note that adjusting the second frequency by adjusting the comb spacing to lock on to the isoclinic point of the second substance also may alter the first frequency, so a sufficient number of feedback iterations may be used to satisfactorily lock on both to the absorption feature of the first substance and the isoclinic point of the second substance. Additionally, note that in alternative embodiments, the control signal from second addition module 59' may be used to control the offset frequency so as to lock on to the isoclinic point of the second substance, and the control signal from first addition module 39' may be used to control the comb spacing so as to lock on to the absorption feature of the first substance.

Alternative system 30' may be configured so as to determine the difference between the first and second frequencies in a manner analogous to that described above with reference to FIG. 3A, e.g., by optically heterodyning the first and second frequencies so as to obtain a beat frequency, obtaining a numerical representation of the beat frequency, and calculating the physical parameter based on the numerical representation and a calibration constant. Alternatively, in the embodiment illustrated in FIG. 3B, calculation module 79' is coupled to laser 31' so as to receive a numerical representation of the laser's comb frequency, e.g., 80 MHz, and is configured to calculate the physical parameter of the first substance within first transmission cell 32' based on the numerical representation of the comb frequency in a manner analogous to that described above with reference to FIG. 3A. Alternatively, calculation module 79' may receive from laser 31' an electronic representation of the laser comb frequency, e.g., an output of a photodetector coupled to the cavity of laser 31', and may include an on-board frequency counter configured to obtain a numerical representation of the comb frequency.

It should be understood that laser 31' need not necessarily be configured to as to generate a frequency comb, but instead may be any suitable laser configured so as to generate a first frequency that may be locked to an absorption feature of the first substance and a second frequency that may be locked to an isoclinic point of the second substance using suitable controller circuitry. In the embodiment illustrated in FIG. 3B, such controller circuitry includes first lock-in amplifier 34', second lock-in amplifier 54', first frequency modulator 35', second frequency modulator 55', first PID controller 36', second PID controller 56', offset frequency controller 37', and comb frequency controller 80'. Additionally, any suitable measurement circuitry configured to determine the difference between the first and second frequencies from laser 31', which in some embodiments may be based on the comb spacing, and to calculate the physical parameter based on the determined difference and a calibration constant. In the embodiment illustrated in FIG. 3B, such measurement circuitry includes calculation module 79'.

Additionally, it should be understood that embodiments such as illustrated in FIGS. 3A and 3B may be based on respectively locking laser frequencies to any suitable transitions of the first and second substances. For example, the second substance may include, or even may consist essentially of, an atomic gas. The absorption spectrum of such an atomic gas may include first and second overlapping peaks that respectively correspond to first and second electronic transitions of the atomic gas, a point in the overlap between the peaks defining an isoclinic point of the atomic gas. In one illustrative example, the gas includes an alkali atomic gas having a nuclear spin of 3/2, e.g., $^{87}$Rb, $^7$Li, $^{23}$Na, $^{39}$K, or $^{41}$K. In such examples, the first and second peaks may correspond to the $5^2S_{1/2}$ ($F_g$=2) to $5^2P_{1/2}$ ($F_e$=1) and the $5^2S_{1/2}$ ($F_g$=2) to $5^2P_{1/2}$ ($F_e$=2) electronic transitions of the gas. However, it should be understood that any substance (including gases, solids, liquids, and plasmas) having an isoclinic point may be used, and that the substance need not necessarily be contained within a transmission cell. In one embodiment, the substance is $^{87}$Rb gas, and is contained within a transmission cell. For further details on isoclinic points of different substances, see the above-mentioned Wells patents.

The first substance of which the physical parameter is being measured may include the same substance as the second substance, or alternatively may include a different substance than the second substance. For example, the first substance may include the same atomic gas as the second substance, and the absorption feature of the first substance may include a third transition of the atomic gas, e.g., a third electronic transition. The first and second substances may be contained in different transmission cells than one another. For example, in the embodiments illustrated in FIGS. 3A-3B, the first and second transmission cells 32', 52' both contain $^{87}$Rb, although first transmission cell 32' also may contain a buffer gas. Alternatively, the first and second substances even may be contained in the same transmission cell as one another. For example, the transmission cell may contain a single substance that has an absorption spectrum that includes both an isoclinic point and an absorption feature that varies based on a physical parameter. Or, for example, the transmission cell may include a mixture of two or more substances, one of which has an isoclinic point, and another of which has an absorption feature that varies based on a physical parameter.

Additionally, note that any suitable type and frequency of absorption feature of the first substance may be used, so long as the difference between a laser frequency locked to that absorption feature and a laser frequency locked to another substance's isoclinic point may be determined. For example, the absorption feature of the first substance may correspond to an atomic electronic transition, a molecular electronic transition, a vibrational transition, a rotational transition, or a rovibrational transition, among others. Preferably, such transition varies based on a physical parameter, such as temperature, pressure, density, phase, or exposure to an electric or magnetic field, so that the physical parameter may be calculated based on the difference between the frequency of the absorption feature corresponding to that transition and the frequency of an isoclinic point of another substance.

Moreover, although not specifically illustrated, it should be understood that systems 30 or 30' respectively illustrated in FIGS. 3A-3B suitably may be modified so as to include adjustment circuitry for adjusting the physical parameter of the first substance based on the physical parameter determined by the measurement circuitry of the respective systems. For example, system 30 may be modified such that first addition module 39 outputs a control signal to a heater coupled to first transmission cell 32, in a manner analogous to that described above with reference to FIG. 1, so as to bring the temperature of the first substance to a desired setpoint.

An exemplary method 40 for measuring a physical parameter of a first substance now will be described with reference to FIG. 4. Although method 40 is explained with reference to the illustrative systems described above with reference FIGS. 3A-3B, it should be understood that method 40 suitably may be modified for use with other types and arrangements of optical and electronic elements.

Figure 4:
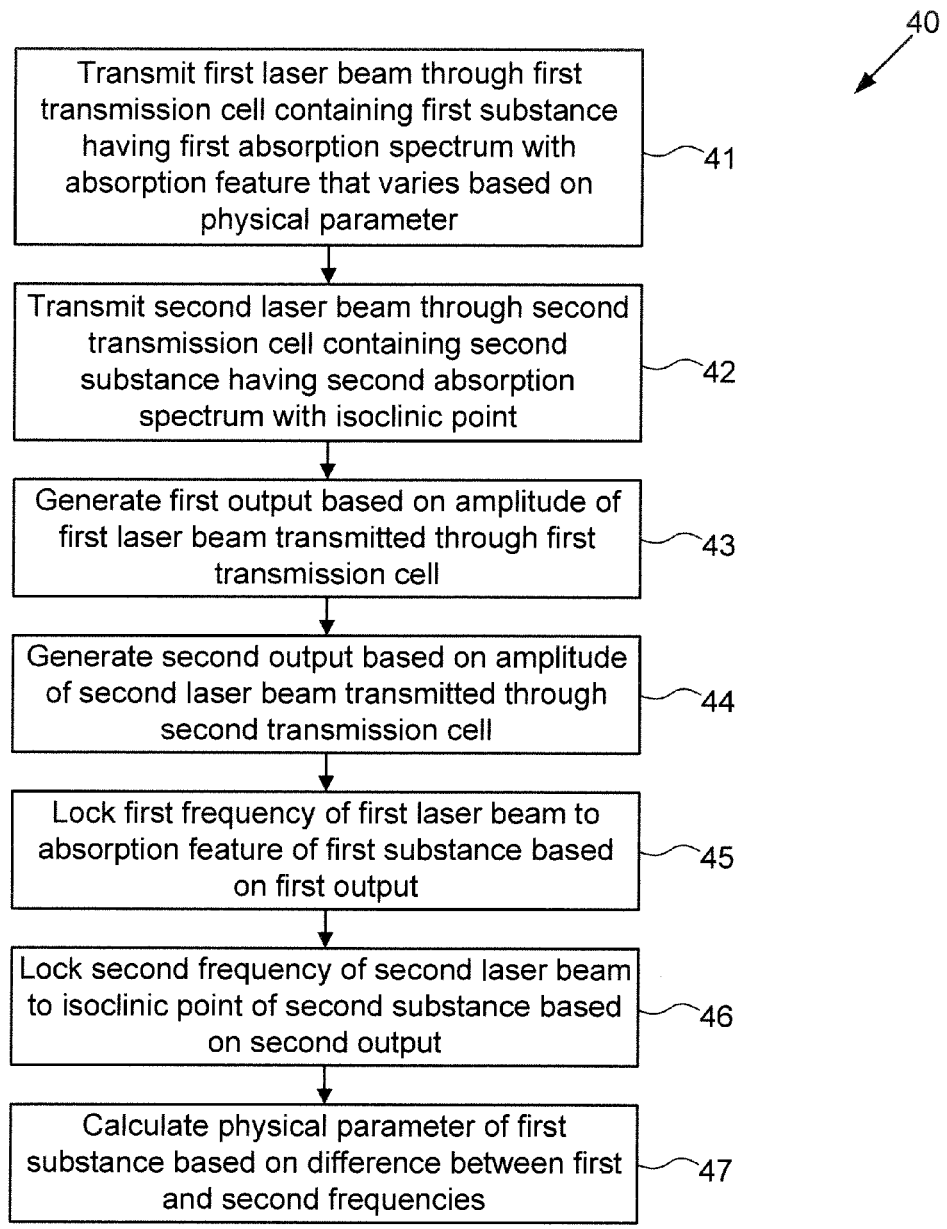
FIG. 4 is a flow chart of steps in an exemplary method for measuring a physical characteristic of a substance based on an isoclinic point in the absorption spectrum of another substance, according to some embodiments of the present invention.

Method 40 illustrated in FIG. 4 includes transmitting a first laser beam through a first transmission cell containing a first substance having a first absorption spectrum with an absorption feature that varies based on a physical parameter (step 41). For example, as illustrated in FIG. 3A, a laser beam from first laser 31 may be reflected or transmitted by any suitable combination of optical elements, e.g., mirrors or beamsplitters, through first transmission cell 32. Or, for example, as illustrated in FIG. 3B, a laser beam of first frequency from laser 31' may be reflected or transmitted by any suitable combination of optical elements, e.g., mirrors or beamsplitters, through first transmission cell 32'.

Method 40 illustrated in FIG. 4 also includes transmitting a second laser beam through a second transmission cell containing a second substance having a second absorption spectrum with an isoclinic point (step 42). For example, as illustrated in FIG. 3A, a laser beam from second laser 51 may be reflected or transmitted by any suitable combination of optical elements, e.g., mirrors or beamsplitters, through second transmission cell 52. Or, for example, as illustrated in FIG. 3B, a laser beam of second frequency from laser 31' may be reflected or transmitted by any suitable combination of optical elements, e.g., mirrors or beamsplitters, through second transmission cell 52'.

Method 40 illustrated in FIG. 4 also includes generating a first output based on an amplitude of the first laser beam transmitted through the first transmission cell (step 43). For example, as illustrated in FIG. 3A, first photodetector 33 may receive laser light transmitted through first transmission cell 32, and may output an electronic representation of the amplitude of the received laser light. Or, for example, as illustrated in FIG. 3B, first photodetector 33' may receive the laser beam of first frequency transmitted through first transmission cell 32', and may output an electronic representation of the amplitude of the received laser light. In either embodiment, the amplitude of the received laser light preferably varies based on the relative frequencies of the laser light and the absorption feature, which in turn varies based on the physical parameter of the first substance.

Method 40 illustrated in FIG. 4 also includes generating a second output based on an amplitude of the second laser beam transmitted through the second transmission cell (step 44). For example, as illustrated in FIG. 3A, second photodetector 53 may receive laser light transmitted through second transmission cell 52, and may output an electronic representation of the amplitude of the received laser light. Or, for example, as illustrated in FIG. 3B, second photodetector 53' may receive the laser beam of second frequency transmitted through second transmission cell 52', and may output an electronic representation of the amplitude of the received laser light. In either embodiment, the amplitude of the received laser light preferably varies based on the relative frequencies of the laser light and the isoclinic point, which preferably does not substantially vary based on the physical parameter of the second substance.

Method 40 illustrated in FIG. 4 further includes locking a first frequency of the first laser beam to an absorption feature of the first substance based on the first output (step 45). For example, as illustrated in FIG. 3A, first lock-in amplifier 34 may receive as input the first output from first photodetector 33, as well as a sinusoidally varying signal from first frequency modulator 35, and may output an error signal based on these two inputs to first PID control 36. First PID control 36 may output to first addition module 39 a control signal based on the error signal. First addition module 39 also may receive the sinusoidally varying signal from first frequency module 35, and may output to first injection current controller 37 a control signal causing the first frequency of first laser 31 to lock to the absorption feature of the first substance. Or, for example, as illustrated in FIG. 3B, first lock-in amplifier 34' may receive as input the first output from first photodetector 33', as well as a sinusoidally varying signal from first frequency modulator 35', and may output an error signal based on these two inputs to first PID control 36'. First PID control 36' may output to first addition module 39' a control signal based on the error signal. First addition module 39' also may receive the sinusoidally varying signal from first frequency module 35', and may output to first injection current controller 37' a control signal causing the first frequency of first laser 31' to lock to the absorption feature of the first substance.

Method 40 illustrated in FIG. 4 further includes locking a second frequency of the second laser beam to an isoclinic point of the second substance based on the second output (step 46). For example, as illustrated in FIG. 3A, second lock-in amplifier 54 may receive as input the second output from second photodetector 53, as well as a sinusoidally varying signal from second frequency modulator 55, and may output an error signal based on these two inputs to second PID control 56. Second PID control 56 may output to second addition module 59 a control signal based on the error signal. Second addition module 59 also may receive the sinusoidally varying signal from second frequency module 55, and may output to second injection current controller 57 a control signal causing the second frequency of second laser 51 to lock to the absorption feature of the second substance. Or, for example, as illustrated in FIG. 3B, second lock-in amplifier 54' may receive as input the second output from second photodetector 53', as well as a sinusoidally varying signal from second frequency modulator 55', and may output an error signal based on these two inputs to second PID control 56'. Second PID control 56' may output to second addition module 59' a control signal based on the error signal. Second addition module 59' also may receive the sinusoidally varying signal from second frequency module 55', and may output to comb frequency controller 80' a control signal causing the comb spacing of second laser 51' to vary so as to lock to the isoclinic point of the second substance.

Method 40 illustrated in FIG. 4 also includes calculating the physical parameter of the first substance based on a difference between the first and second frequencies (step 47). For example, as illustrated in FIG. 3A, third photodetector 73 may receive an optical heterodyne of the first and second frequencies, and may provide to frequency counter 78 a third output based on the beat frequency between the first and second frequencies. Frequency counter 78 provides a numerical representation of the beat frequency to calculation module 79, which may calculate the physical parameter of the first substance based on the numerical representation and a calibration constant. Or, for example, as illustrated in FIG. 3B, calculation module 79' may obtain a numerical representation of the comb frequency from laser 31' (or an electronic representation of the comb frequency from which module 79' may obtain a numerical representation of the comb frequency), and may calculate the physical parameter of the first substance based on the numerical representation and a calibration constant.

Note that the systems and methods described above with reference to FIGS. 3A-3B and 4 are merely illustrative, and should not be construed as limiting. Indeed, many suitable types and arrangements of optical and electronic elements, and uses thereof to measure the physical parameter of a substance based on an isoclinic point of another substance, may be envisioned.

Figure 5:
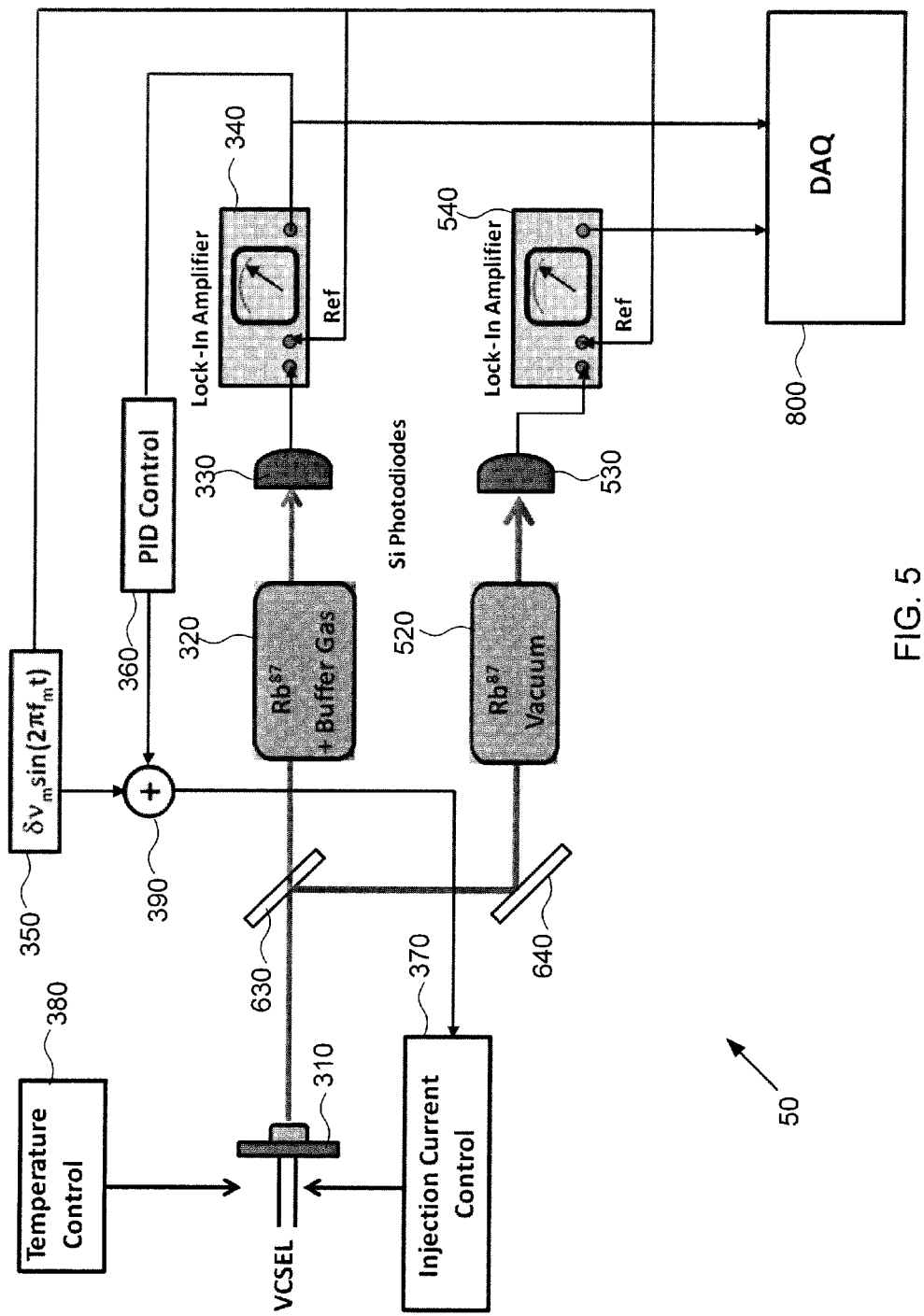
FIG. 5 illustrates another alternative exemplary system for measuring a physical characteristic of a substance based on an isoclinic point in the absorption spectrum of another substance, according to some embodiments of the present invention.

For example, FIG. 5 illustrates another exemplary system 50 that suitably may be used to measure a physical parameter of a substance based on an isoclinic point of another substance. System 50 includes laser 310, first transmission cell 320 containing a first substance, second transmission cell 520 containing a second substance, first photodetector 330, second photodetector 530, beamsplitter 630, mirror 640; controller circuitry that includes first lock-in amplifier 340, second lock-in amplifier 540, frequency modulator 350, PID controller 360, injection current controller 370, laser temperature controller 380, and addition module 390; and measurement circuitry that includes data acquisition card (DAQ) 800.

In the embodiment illustrated in FIG. 5, laser 310 is any suitable laser, including a continuous-wave (CW) or pulsed laser, the frequency of which is tunable via any suitable mechanism. In one illustrative embodiment, laser 310 is a diode laser, e.g., a vertical-cavity surface emitting laser (VCSEL), the frequency of which is tunable by adjusting the driver current applied to the diode via injection current controller 370 while holding the temperature of the diode constant using laser temperature controller 380 in a manner analogous to that described above with reference to FIG. 3A. Alternatively, the frequency of laser 310 may be tuned using any suitable combination of driver current via injection current controller 370 and temperature via laser temperature controller 380.

Beamsplitter 630 transmits a portion of the light from laser 310 towards and through first transmission cell 320 containing a first substance having a first absorption spectrum with an absorption feature that varies based on a physical parameter, e.g., a mixture of $^{87}$Rb and a buffer gas, and then onto first photodetector 330. Beamsplitter 630 reflects another portion of the light from laser 310 towards mirror 640, which reflects the light through second transmission cell 520 containing a second substance having a second absorption spectrum with an isoclinic point, e.g., $^{87}$Rb "in vacuum," and then onto second photodetector 530. It should be appreciated that other optical arrangements suitably may be used.

First photodetector 330, which in the illustrated embodiment is a silicon (Si) based photodiode, is configured to generate a first output based on an intensity of the light from laser 310 transmitted through first transmission cell 320, which in turn depends on the physical parameter of the first substance. First photodetector 330 is configured to provide the first output to lock-in amplifier 340, which also is coupled to receive input from frequency modulator 350 and to provide an output to first PID controller 360, which are both configured to provide outputs to first addition module 390, which in turn is configured to output a control signal to injection current controller 370 in a manner analogous to that described above with reference to FIG. 3A. Addition module 390 generates and transmits to injection current controller 370 a control signal based on the adjustment signal and the sinusoidally varying signal from frequency modulator 350 that brings the frequency of laser 310 closer to—and eventually to lock on to—an absorption feature of the substance within first transmission cell 320, using known feedback loop algorithms and techniques. Additionally, the error signal from first lock-in amplifier 340 is provided to DAQ 800.

As noted above, beamsplitter 630 and mirror 640 reflect another portion of the light from laser 310 through second transmission cell 520. Second photodetector 530, which in the illustrated embodiment is a silicon (Si) based photodiode, is configured to generate a second output based on an intensity of the light transmitted through second transmission cell 520. Second photodetector 530 is configured to provide the second output to second lock-in amplifier 540, which also is coupled to receive input from frequency modulator 350 and to provide an output to DAQ 800.

DAQ 800 is configured to calculate the physical parameter of the first substance based on the error signals received from first and second lock-in amplifiers 340, 540. For example, after the frequency of laser 310 is locked to the absorption feature of the first substance, the error signal from first lock-in amplifier 340 may be at a minimum. However, the error signal from second lock-in amplifier 540 may have an amplitude that depends on the frequency of laser 310 relative to absorption features in the absorption spectrum of the second substance. For example, if the laser frequency coincides with an absorption peak of the second substance, then the error signal from second lock-in amplifier 540 may be relatively low, while if the laser frequency coincides with an absorption minimum of the second substance, then the error signal from second lock-in amplifier 540 may be relatively high, while if the laser frequency coincides with a point along the slope of an absorption peak of the second substance, then the error signal may be somewhere between low and high values.

Preferably, within the laser frequency range of operational interest, DAQ 800 may uniquely determine the laser frequency based on the amplitude of the error signal from second lock-in amplifier 540 and on the absorption spectrum of the second substance. In particular, the laser frequency range preferably falls within a region of the absorption spectrum of the second substance that has a relatively steep slope, so that relatively small changes in laser frequency may cause a relatively large change in the error signal from second lock-in amplifier 540. Additionally, such a region of the absorption spectrum of the second substance further does not vary significantly based on changes in the physical parameter, e.g., is sufficiently close to the isoclinic point of the second substance so as to remain relatively stable over changes in the physical parameter over operational ranges of interest. DAQ 800 further may be configured to determine the physical parameter of the first substance based on the determined laser frequency and on a calibration constant in a manner analogous to that described above with reference to FIG. 3A. An exemplary method for calibrating system 50 is described further below in the Examples section.

Moreover, although not specifically illustrated, it should be understood that system 50 illustrated in FIG. 5 suitably may be modified so as to include adjustment circuitry for adjusting the physical parameter of the first substance based on the physical parameter determined by the measurement circuitry of system 50, e.g., DAQ 800. For example, system 50 may be modified such that addition module 390 outputs a control signal to a heater coupled to first transmission cell 320 in a manner analogous to that described above with reference to FIG. 1, so as to bring the temperature of the first substance to a desired setpoint.

An exemplary method 60 for measuring a physical parameter of a first substance now will be described with reference to FIG. 6. Although method 60 is explained with reference to the illustrative system 50 described above with reference FIG. 5, it should be understood that method 60 suitably may be modified for use with other types and arrangements of optical and electronic elements.

Figure 6:
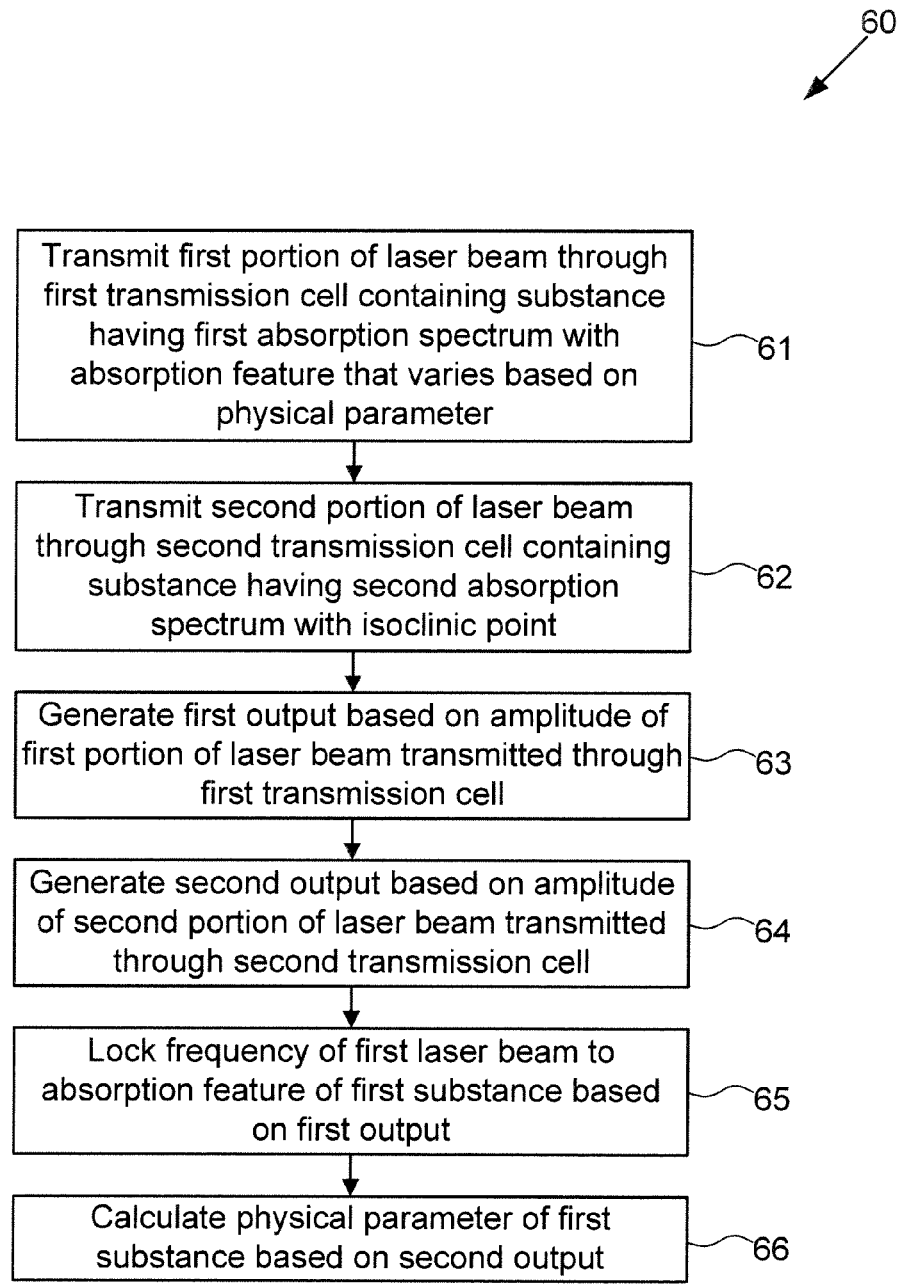
FIG. 6 is a flow chart of steps in an alternative exemplary method for measuring a physical characteristic of a substance based on an isoclinic point in the absorption spectrum of another substance, according to some embodiments of the present invention.

Method 60 illustrated in FIG. 6 includes transmitting a first portion of a laser beam through a first transmission cell containing a first substance having a first absorption spectrum with an absorption feature that varies based on a physical parameter (step 61). For example, as illustrated in FIG. 5, a portion of a laser beam from laser 310 may be reflected or transmitted by any suitable combination of optical elements, e.g., mirrors or beamsplitters, through first transmission cell 320.

Method 60 illustrated in FIG. 6 also includes transmitting a second portion of a laser beam through a second transmission cell containing a second substance having a second absorption spectrum with an isoclinic point (step 62). For example, as illustrated in FIG. 5, a portion of the laser beam from laser 310 may be reflected or transmitted by any suitable combination of optical elements, e.g., mirrors or beamsplitters, through second transmission cell 520.

Method 60 illustrated in FIG. 6 also includes generating a first output based on an amplitude of the first portion of the laser beam transmitted through the first transmission cell (step 63). For example, as illustrated in FIG. 5, first photodetector 330 may receive laser light transmitted through first transmission cell 320, and may output an electronic representation of the amplitude of the received laser light. The amplitude of the received laser light preferably varies based on the relative frequencies of the laser light and the absorption feature, which in turn varies based on the physical parameter of the first substance.

Method 60 illustrated in FIG. 6 also includes generating a second output based on an amplitude of the second portion of the laser beam transmitted through the second transmission cell (step 64). For example, as illustrated in FIG. 5, second photodetector 530 may receive laser light transmitted through second transmission cell 520, and may output an electronic representation of the amplitude of the received laser light. In either embodiment, the amplitude of the received laser light preferably varies based on the relative frequencies of the laser light and the absorption spectrum of the second substance.

Method 60 illustrated in FIG. 6 further includes locking a frequency of the first laser beam to an absorption feature of the first substance based on the first output (step 65). For example, as illustrated in FIG. 5, first lock-in amplifier 340 may receive as input the first output from first photodetector 330, as well as a sinusoidally varying signal from frequency modulator 350, and may output an error signal based on these two inputs to first PID control 360. First PID control 360 may output to first addition module 390 a control signal based on the error signal. First addition module 390 also may receive the sinusoidally varying signal from frequency module 350, and may output to first injection current controller 370 a control signal causing the frequency of laser 310 to lock to the absorption feature of the first substance.

Method 60 illustrated in FIG. 6 further includes calculating the physical parameter of the first substance based on the second output (step 66). For example, as illustrated in FIG. 5, second lock-in amplifier 540 may receive as input the second output from second photodetector 530, as well as a sinusoidally varying signal from frequency modulator 350, and may output an error signal based on these two inputs to DAQ 800, which may determine the laser frequency based on the error signal, and may calculate the physical parameter of the first substance based on the determined laser frequency and a calibration constant.

Note that various components described herein suitably may be implemented using commercially available components or may be integrated into one or more discrete electronics modules, field-programmable gate arrays (FPGAs), application-specific integrated circuits (ASICs), or any suitable combination thereof. For example, PID controllers are commercially available from, e.g., Stanford Research Systems, Inc. (Sunnyvale, Calif.), such as the SIM 960 analog 100 kHz PID controller. Diode lasers may be controlled using temperature and current, and suitable modules are commercially available from, e.g., Newport Corporation (Irvine, Calif.), Stanford Research Systems, Inc., or Wavelength Electronics, Inc. (Bozeman, Mont.). Addition modules such as summing preamplifiers are commercially available from, e.g., Stanford Research Systems, Inc., such as the SIM 980 1 MHz analog summing amplifier, SIM 910 JFET preamplifier, or SR560 low-noise voltage preamplifier. Frequency counters in the radio frequency (RF) range are commercially available from, e.g., Hewlett-Packard Company (Palo Alto, Calif.), Agilent Technologies, Inc. (Santa Clara, Calif.), or Teledyne LeCroy (Chestnut Ridge, N.Y.), and suitably may range from 10 MHz to 40 GHz, for example. Comb frequency controllers and offset frequency controllers suitably may be selected based on the type of laser being used; for example, the offset frequency of a Ti:sapphire laser oscillator suitably may be controlled by adjusting the pump diode power, and the cavity length suitably may be controlled using a piezo-mounted end mirror. Calculation modules for use in calculating a physical parameter of a substance may be implemented using a data acquisition board and any suitable combination of hardware and software, e.g., using an FPGA or ASIC.

An overview of isoclinic points now will be provided, and thereafter some experimental results obtained using systems such as illustrated in FIGS. 3A-3B and 5 and methods such as illustrated in FIGS. 4 and 6 will be described.

Isoclinic Points

As discussed in greater detail in U.S. Pat. Nos. 8,050,301 and 8,442,083 to Wells et al., the entire contents of both of which are incorporated by reference herein, the absorption spectra of some gases contain isoclinic points to which a laser may be locked, and that do not substantially change in frequency as a function of physical parameters, such as temperature, pressure, density, phase, or exposure to an electric or magnetic field. As used herein, an isoclinic point is defined as "[a] wavelength, wavenumber, or frequency at which the first derivative of an absorption spectrum of a sample does not change upon a chemical reaction or physical change of the sample." Such a definition is the same as that defined by the International Union of Pure and Applied Chemistry (IUPAC), see *Compendium of Chemical Terminology*, $2^{nd}$ ed. (the "Gold Book"), Oxford (1997). As described in the above-mentioned Wells patents, isoclinic points exist for alkali atoms with nuclear spin I equal to 3/2, and that the frequencies of these isoclinic points are effectively independent of physical parameters such as temperature. That is, the derivative $dv_o/dT$ at the isoclinic point is spectroscopically insignificant, where $\rho_0$ is the frequency at the isoclinic point and T is the gas temperature. The sensitivity of the alkali's isoclinic points to laser linewidth and optical pumping efficiency are also discussed in the Wells patents. It should be appreciated that although the discussion below is primarily directed to gases containing alkali atoms, that other types of atoms or molecules, including those in non-gas states, may also have absorption spectra with isoclinic points.

As noted above with respect to FIGS. 2A-2B, peaks corresponding to electronic transitions may be Doppler broadened, leading to overlap that may cause a laser frequency to be pulled away from a desired frequency. To illustrate the problem more quantitatively, consider two neighboring Doppler-broadened transitions, A and B, such as those illustrated in FIG. 2B, where $w_D$ is the Doppler-broadened full-width half-maximum (FWHM) of either peak A or B. For a laser of frequency $\omega_L$ tuned near these absorption lines, the intensity I transmitted by a gas of length L can be expressed as:

$$I(L)=I_o\exp[-NL[\sigma_A(\Delta_A)+\sigma_B(\Delta_B)]], \quad (1)$$

where $\sigma_J(\Delta_J)$ is the cross section of the $J^{th}$ resonance and $\Delta_J$ is the detuning from the true resonant frequency of the transition: $\Delta_J=\omega_L-\omega_J$. Taking the derivative of Eq. (1) with respect to laser frequency $\omega_L$ and setting this equal to zero, we find the extrema in the absorption spectrum:

$$\frac{dI(L)}{d\omega_L} = -NLe^{-N[\sigma_A(\Delta_A)+\sigma_B(\Delta_B)]L}\left(\frac{d\sigma_A}{d\omega_L} + \frac{d\sigma_B}{d\omega_L}\right) = \quad (2)$$
$$0 \implies \left(\frac{d\sigma_A}{d\omega_L} + \frac{d\sigma_B}{d\omega_L}\right) = 0.$$

For the case of the extremum near absorption line A, this yields the peak frequency of the A transition:

$$\omega_{pA} = \omega_A - \Delta_B\left(\frac{\sigma_{pB}}{\Delta_{pA}}\right)e^{-4ln(2)\left(\frac{\Delta_B}{w_D}\right)^2} \cong \quad (3)$$
$$\omega_A - (\omega_A - \omega_B)\left(\frac{\sigma_{pB}}{\sigma_{pA}}\right)e^{-4ln(2)\left(\frac{(\omega_A-\omega_B)}{w_D}\right)^2},$$

where $\sigma_{pJ}$ is the peak absorption cross section of the $J^{th}$ transition, and where $\omega_{pA}$ is seen to have a temperature dependent shift due to the temperature sensitivity of the Doppler width. To be clear, $\omega_{pA}$ is the peak frequency of the absorption line A, while $\omega_A$ is the intrinsic resonant frequency of the transition, e.g., the $5^2S_{1/2}$ ($F_g=2$) to $5^2P_{1/2}$ ($F_e=1$) transition for $^{87}$Rb. In particular, for small changes about some reference temperature $T_o$, and defining $\Delta_{AB}$ as $\omega_A-\omega_B$, the peak frequency of the transition will vary as $$\frac{\delta\omega_{pA}}{\delta T} = -4ln(2)\frac{\Delta_{AB}}{T_o}\left(\frac{\sigma_B(\Delta_{AB})}{\sigma_{pA}}\right)\left(\frac{\Delta_{AB}}{w_D(T_o)}\right)^2. \quad (4)$$

Figure 2A:
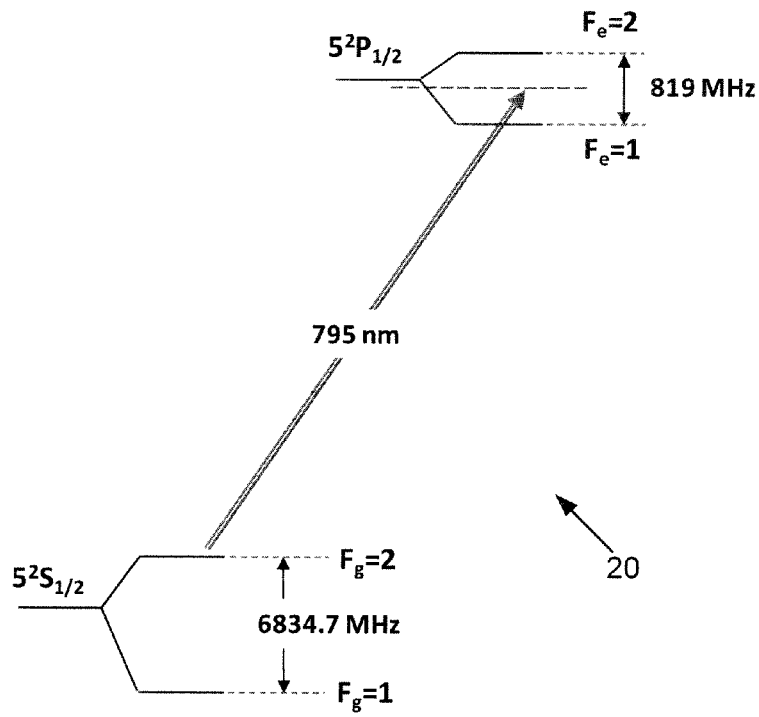
FIG. 2A schematically illustrates the electronic transitions of $^{87}$Rb.
Figure 2B:
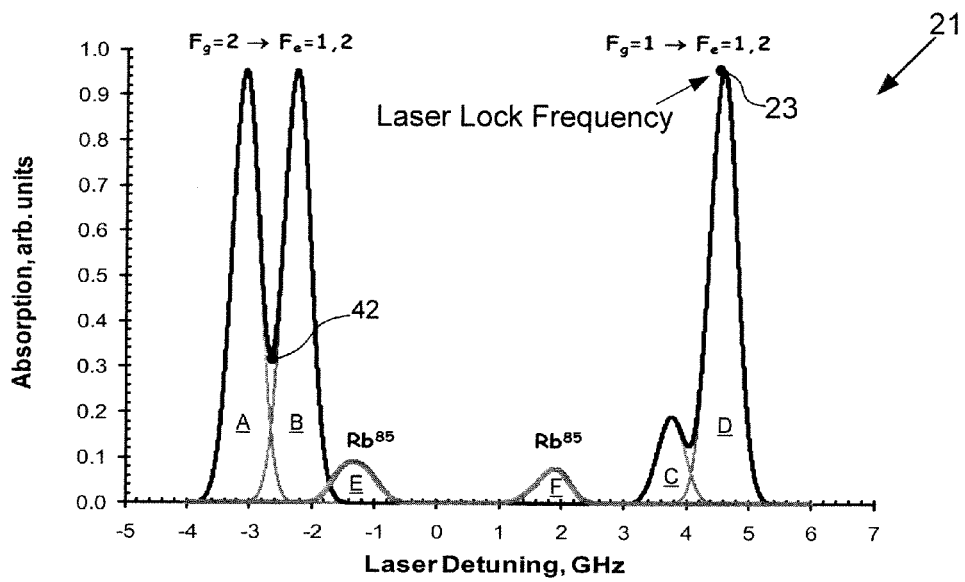
FIG. 2B is a plot of the calculated atomic absorption spectrum of $^{87}$Rb as a function of laser detuning frequency.

For absorption line A in FIG. 2B near room temperature this yields $\delta\omega_{pA}/\delta T \cong 16$ kHz/° C. or in fractional frequency, y, $4.2\times10^{-11}$/° C. (i.e., $y\equiv\delta\omega/\omega_o$). This is a relatively large temperature sensitivity, and demonstrates the significance of temperature variations for precision vapor-phase spectroscopy.

As described in greater detail in the above-incorporated Wells patents, the temperature dependence indicated by Eq. (4) may arise from the fact that, near an absorption line's peak, one of the cross-section derivatives becomes effectively independent of temperature while the other retains its Doppler-broadening temperature sensitivity. Conversely, near the midpoint between the two resonances, both derivatives are temperature dependent. In particular, if $\omega_m$ is defined to be the frequency corresponding to the local extremum near the midpoint, then for reasonably well-resolved, Doppler-broadened absorption lines, $$\omega_m \cong \left(\frac{\omega_A + \omega_B}{2}\right) - \frac{(\sigma_{pA} - \sigma_{pB})}{(\sigma_{pA} + \sigma_{pB})} \frac{\Delta_{AB} w_D^2}{4\ln(2)\Delta_{AB}^2 - 2w_D^2}. \quad (5)$$

In this case, the temperature dependence of the extremum only arises when the absorption cross-sections of the two transitions are unequal. When $\sigma_{pA}$ equals $\sigma_{pB}$, the second term on the right-hand-side of Eq. (5) is identically zero, and the frequency of the local extremum equals the intrinsic midpoint frequency of the two transitions independent of temperature: it is an isoclinic point.

Notwithstanding the above discussion, for precision spectroscopy it is important to note that isoclinic points are idealizations. As described in the Wells patents, it is unlikely that any given gas-phase atomic or molecular spectral feature will ever be insensitive to a "physical change of the sample" to all orders. For example, in real systems, alkali isotopes often co-exist, and even in a vapor of "pure" $^{87}$Rb there is always some fractional component of $^{85}$Rb (e.g., 10% residual $^{85}$Rb) with absorption lines E, F that overlap (albeit slightly) those of $^{87}$Rb, as illustrated in FIG. 2B. This overlap implies that Eq. (1) may be augmented with a third absorption cross-section, complicating the simple argument leading to Eq. (5). Moreover, because single mode lasers may be dominated by white frequency fluctuations, producing Lorentzian laser spectra with corresponding long tails, there also may be an interaction between $^{85}$Rb contamination and laser linewidth. Finally, an alignment among the ground-state Zeeman sub-levels produced by optical pumping may degrade the equality between the A and B cross-sections, thereby giving the isoclinic point an alternate path to temperature sensitivity. As noted in the Wells patents, the presence of residual $^{85}$Rb may cause the frequency of the isoclinic point to vary with temperature; however the extent of such variation is expected to be significantly smaller than that for the maximum of an absorption peak. Issues associated with residual $^{85}$Rb are described in further detail in the Wells Patents.

As may be derived from prior art atomic physics theory, the peak cross section for a $D_1$ transition in the alkalies (i.e., excited and ground state electronic angular momenta, $J_e$ and $J_g$, respectively, equal to ½) originating from the $F_g$=I+½ ground-state hyperfine manifold (where I is the nucleus's spin angular momentum quantum number) may be expressed as $$\sigma_p(F_g, F_e) = \sigma_o[J_g]\left(1 + \frac{2\langle \vec{I} \cdot \vec{S} \rangle}{\langle I+1 \rangle}\right)\begin{cases} \frac{(2I+3)(I+1)}{6(2I+1)^2}; & F_e = I + \frac{1}{2} \\ \frac{2I(I+1)}{3(2I+1)^2}; & F_e = I - \frac{1}{2} \end{cases}, \quad (6)$$

where $<\vec{I} \cdot \vec{S}>$ is a measure of ground-state hyperfine polarization (e.g., the population imbalance between the two ground-state hyperfine levels) and $\sigma_o$ is the integrated $D_1$ absorption cross section (the expressions herein use the notation $[J]\equiv(2J+1)$.) Employing the second approximation of Whiting, J. Quant. Spectrosc. Radiat. Transfer 8, 1379-1384 (1968), the entire contents of which are incorporated by reference herein, for a Voigt profile, the functional relationship between o and the transition's oscillator strength, f, can be obtained:

$$\sigma_o = \frac{2\pi^2 r_o f c}{w_V\left[1.065 + 0.447\left(\frac{w_L}{w_V}\right) + 0.058\left(\frac{w_L}{w_V}\right)\right]}, \quad (7)$$

where $r_o$ is the classical electron radius. The values $w_L$, $w_D$, and $w_V$ correspond to the FWHM of the Lorentzian, Doppler, and Voigt profiles, respectively, and are related by:

$$w_V = \frac{w_L}{2} + \sqrt{\frac{w_L^2}{4} + w_D^2}. \quad (8)$$

Similarly, for the $D_1$ transition originating from the $F_g$=I−½ hyperfine manifold, $$\sigma_p(F_g, F_e) = \sigma_o[J_g]\left(1 - \frac{2\langle \vec{I} \cdot \vec{S} \rangle}{I}\right)\begin{cases} \frac{2I(I+1)}{3(2I+1)^2}; & F_e = I + \frac{1}{2} \\ \frac{I(2I-1)}{6(2I+1)^2}; & F_e = I - \frac{1}{2} \end{cases}. \quad (9)$$

Writing Whiting's second approximation for the Voigt profile in detail, the frequency dependence of the absorption cross-sections may be expressed as $$\sigma_{F_g, F_e}(\Delta_J) = \quad (10)$$

$$\sigma_p(F_g, F_e)\left\{\left[1 - \frac{w_L}{w_V}\right]e^{-4\ln(2)\left(\frac{\Delta_J}{w_V}\right)^2} + \left[\frac{w_L}{w_V}\right]\left(\frac{1}{1 + 4\left(\frac{\Delta_J}{w_V}\right)^2}\right) + \frac{1}{62.5}\left[1 - \frac{w_L}{w_V}\right]\left[\frac{w_L}{w_V}\right]\left(e^{-0.4\left(\frac{|\Delta_J|}{w_V}\right)^{\frac{9}{4}}} - \frac{10}{10 + \left(\frac{|\Delta_J|}{w_V}\right)^{\frac{9}{4}}}\right)\right\},$$

where the index J corresponds to one of the $F_g \rightarrow F_e$ resonances illustrated in FIGS. 2A-2B.

Note that the two cross sections originating from the $F_g$=I+½ ground-state hyperfine manifold (expressed by Eq. (6)) will be equal when I=3/2, corresponding to the stable alkali isotopes Li, $^{23}$Na, $^{39}$K, $^{41}$K, and $^{87}$Rb. Thus, there will be an isoclinic point midway between these transitions. Table I lists the $D_1$ transition properties of various alkali isotopes that it is believed would show an isoclinic point at an extremum of the $n^2S_{1/2}(F_g=2)\rightarrow n^2P_{1/2}$ ($F_e$=1,2) transitions. The temperatures were chosen to produce a vapor density of $10^{10}$ cm$^{-3}$, and $\Delta\nu_{hfs}$ corresponds to the hyperfine splitting in the $n^2P_{1/2}$ (first resonance) state. Note that only in the case of $^{87}$Rb will the two $D_1$ transitions be resolved relative to the Doppler width, which is given in the last column. Of these isotopes, as shown in Table I, $^{87}$Rb produces the largest vapor densities at the lowest temperatures, which may be particularly useful for UAP applications. Conversely, the two peak cross sections originating from the $F_g$=I−½ ground-state hyperfine manifold (expressed by Eq. (9)) are only equal for the unphysical case of I=−5/2. Thus, for the $D_1$ transition of the alkalies, excitation from $F_g=I-\frac{1}{2}$ will not yield an isoclinic point at an extremum of the absorption cross section. For further details, see the above-incorporated Wells patents.

TABLE I

| Alkali | Abundance | 1st Resonance λ D₁, nm | $\Delta v_{hfs}$, MHz | T, °C. | $\Delta v_D$, MHz |
|---|---|---|---|---|---|
| ⁷Li | 93% | 670.8 | 92 | 291 | 2872 |
| ²³Na | 100% | 589.6 | 189 | 114 | 1494 |
| ³⁹K | 93% | 769.9 | 58 | 53 | 806 |
| ⁴¹K | 7% | 769.9 | — | 53 | 786 |
| ⁸⁷Rb | 28% | 794.8 | 812 | 25 | 500 |

As described in the Wells patents, for ⁸⁷Rb, the change in frequency with temperature of the maximum of peak D is several orders of magnitude higher than that of isoclinic point 42 illustrated in FIG. 2B. The presence of residual ⁸⁵Rb (here, 1% ⁸⁵Rb) may cause a small amount of pulling away from isoclinic point 42, leading to some variation in frequency as a function of temperature. However, even with such variation, the isoclinic point is believed to be substantially stable over a range of useful range of physical parameters as compared to an absorption peak maximum, such as that of peak D illustrated in FIG. 2B.

Experiment

The sensitivity of system 30 illustrated in FIG. 3A to measure changes in the temperature of a gas was experimentally measured. The experimental system was analogous to that illustrated in FIG. 3A, except that both first transmission cell 32 and second transmission cell 52 contained approximately 10⁻⁴ Torr of ⁸⁷Rb "in vacuum," that is, without use of a buffer gas in either cell. The frequency of first laser 31 was locked to an absorption peak corresponding to the $5^2S_{1/2}$ ($F_g=2$) →$5^2P_{1/2}$ ($F_e=2$) transition, which is a temperature-sensitive transition, of the ⁸⁷Rb in first transmission cell 32. The frequency of second laser 51 was locked to the isoclinic point of the ⁸⁷Rb in the second transmission cell 52.

Figure 7A:
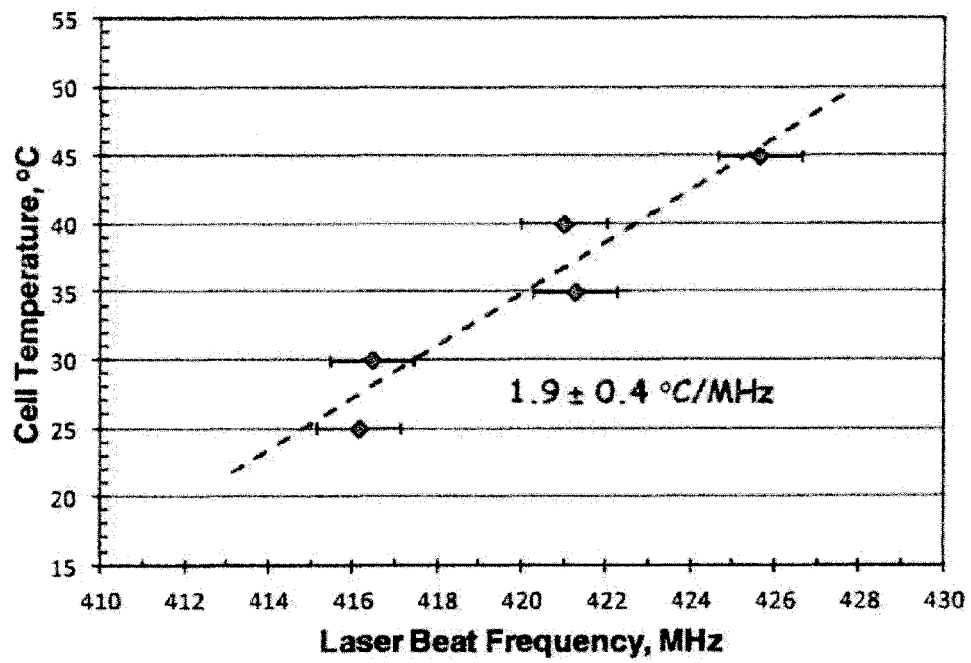
FIG. 7A is a plot of changes in gas cell temperature as a function of beat frequency measured during an experiment using the system illustrated in FIG. 3A, according to some embodiments of the present invention.

In a first experiment, the temperature of the first transmission cell 32 was varied using a heater (not shown), the temperature of the second transmission cell 52 was held steady, and the beat frequency between the first and second lasers 31, 51 was measured using photodetector 73 and frequency counter 78. FIG. 7A illustrates a plot of the measured beat frequency as a function of the temperature of first transmission cell 32. It may be seen that as the cell temperature increased, the beat frequency also increased, from approximately 416 MHz at a temperature of 25° C. to approximately 426 MHz at a temperature of 45° C. The sensitivity of the system to measure changes in the temperature of the ⁸⁷Rb in first transmission cell 32 may be determined from the slope of the best-fit line through the measured points, shown as a dashed line in FIG. 7A, and was found to be approximately 1.9±0.4° C./MHz. Such a slope may be utilized as a calibration constant from which calculation module 79 may calculate the temperature of the ⁸⁷Rb in first transmission cell 32 based upon the measured beat frequency.

Note that although the calibration constant determined during this particular experiment has a relatively large error, it is believed that such an error arose from a relatively high level of noise on the lasers 31, 51 and also because the beat frequency was averaged for only a few seconds. Nonetheless, even with such a level of laser noise and averaging time, FIG. 7A demonstrates that temperature variations at the level of 1° C. readily may be measured. It is believed that by averaging the beat frequency for a longer amount of time, e.g., over 100 seconds (which is fast on the time scale of temperature variations), and by reducing laser noise, the beat frequency may be measured with significantly greater accuracy. In particular, diode lasers operating at about 795 nm have been stabilized to frequencies of 500 Hz for averaging times of 100 seconds from Doppler-broadened resonances. This would imply a beat note frequency error of about 700 Hz from two independent lasers, corresponding to an ability to sense and control actual temperature variations in a transmission cell at the level of 10⁻³° C.

Figure 7B:
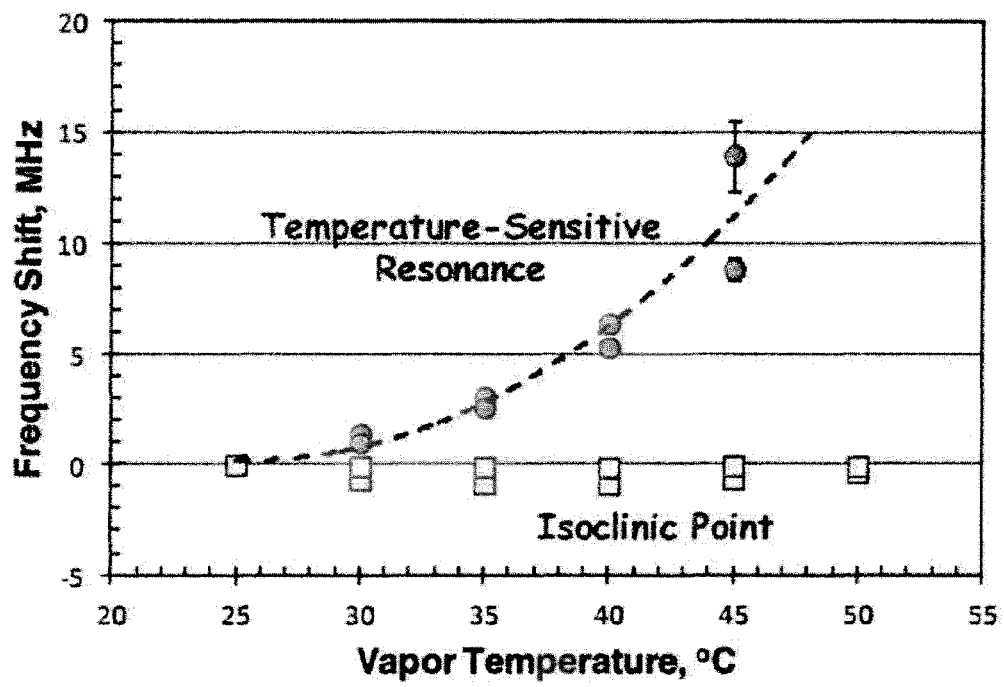
FIG. 7B is a plot of respective frequency shift as a function of temperature for a temperature-sensitive absorption feature and an isoclinic point measured during an experiment using the system illustrated in FIG. 3A, according to some embodiments of the present invention.

In another experiment, the respective temperature sensitivities of the temperature-sensitive resonance of the ⁸⁷Rb in first transmission cell 32 and the isoclinic point of the ⁸⁷Rb in second transmission cell 52 were measured by determining the frequency shift of such absorption features as a function of temperature. Specifically, the temperatures of the first and second transmission cells 32, 52 were varied using respective heaters, and the frequencies of lasers 31 and 51 were unlocked. The laser frequency that respectively produced a zero error signal from lock-in amplifiers 34, 54 was measured. Note that such a laser frequency corresponds to the absorption lineshape's first derivative, although for the present experiment the zero of the lineshape's third derivative equivalently was used so as to reduce the effects of laser amplitude modulation arising from the modulation of the lasers' driver currents. FIG. 7B illustrates a plot of the frequency shifts of the temperature-sensitive resonance of the ⁸⁷Rb within first transmission cell 32 and the isoclinic point of the ⁸⁷Rb within second transmission cell 52. It may be seen that from a nominal frequency of about 0 MHz at a temperature of 25° C., the temperature-sensitive resonance of the ⁸⁷Rb within first transmission cell 32 shifted by nearly 15 MHz at a temperature of 45° C. In comparison, it may be seen that the isoclinic point of the ⁸⁷Rb within second transmission cell 52 substantially did not shift from its nominal frequency of about 0 MHz within the temperature range tested in this experiment. Thus, it may be seen that within at least the shown operational range, the frequency of the isoclinic point substantially did not vary, while the frequency of the temperature-sensitive resonance varied significantly.

Figure 8A:
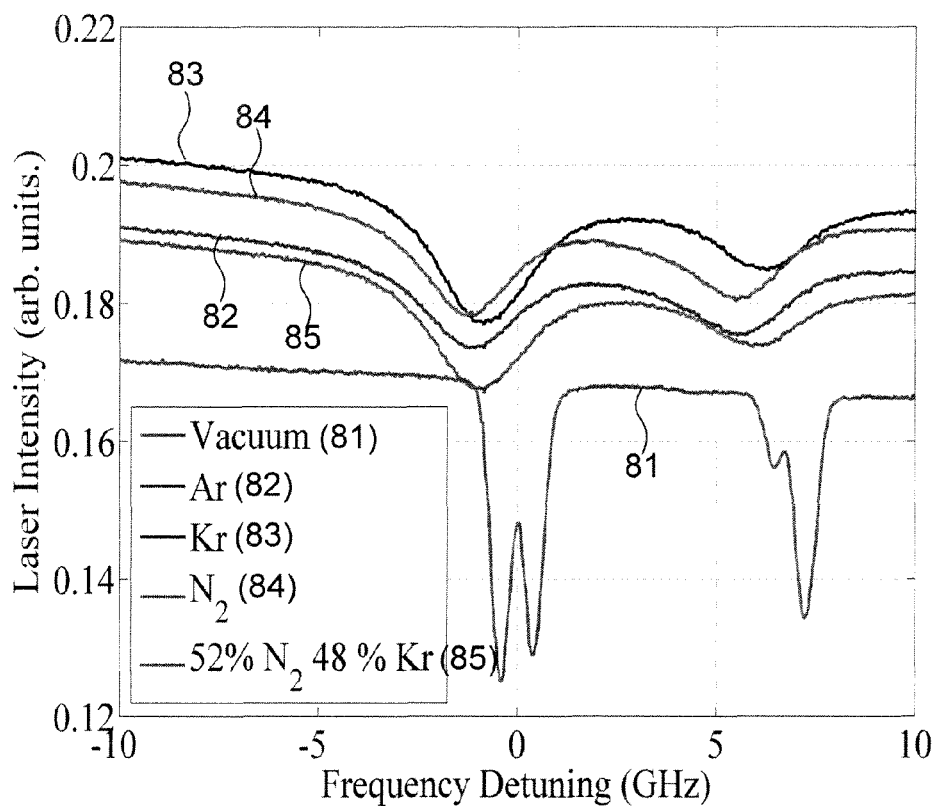
FIG. 8A is a plot of laser intensity as a function of frequency detuning for several different substances measured during an experiment using the system illustrated in FIG. 3A, according to some embodiments of the present invention.

In another series of experiments, the first transmission cell 32 of the above-described experimental setup was modified so as to include different gas mixtures that included approximately 10⁻⁴ Torr of ⁸⁷Rb and either a "vacuum" or a few tens of Torr of a buffer gas consisting either of argon (Ar), krypton (Kr), nitrogen ($N_2$), or a mixture of 52% $N_2$ and 48% Kr, In one experiment, the frequency of first laser 31 first was locked to a nominal frequency of 0 GHz at the isoclinic point of the ⁸⁷Rb in vacuum, and then varied (detuned) from −10 GHz below to +10 GHz above the nominal frequency, while the output from first photodetector 33, e.g., the laser intensity transmitted through first transmission cell 32, was measured. FIG. 8A illustrates a plot of the measured laser intensity as a function of frequency detuning for the above noted gas mixtures, e.g., of the respective absorption spectra of such mixtures. It may be seen that the ⁸⁷Rb in vacuum was determined to have an absorption spectrum 81 that includes the absorption features described further above with reference to FIG. 2B. The respective absorption spectra 82, 83, 84, and 85 of the mixtures of ⁸⁷Rb with Ar, Kr, $N_2$, or $N_2$ and Kr may be seen to have absorption features that are significantly broadened relative to those of the ⁸⁷Rb in vacuum.

Figure 8B:
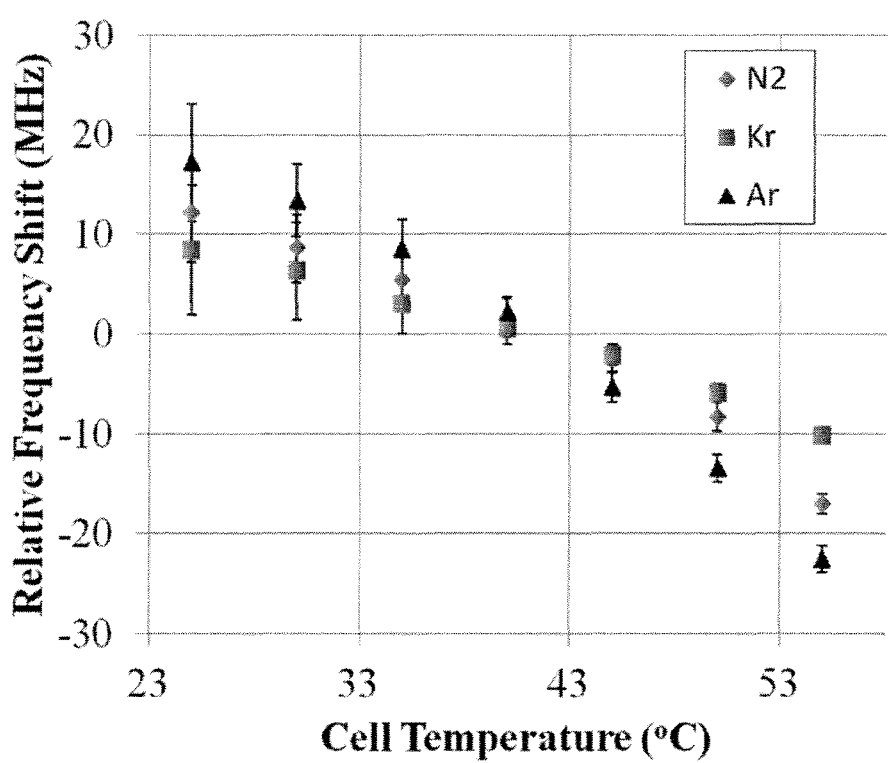
FIG. 8B is a plot of relative frequency shift as a function of cell temperature for several different substances measured during an experiment using the system illustrated in FIG. 3A, according to some embodiments of the present invention.

In another experiment, the temperature of the first transmission cell 32 was varied using a heater (not shown) and the relative frequency shift of the broad absorption peak closest to the nominal frequency was measured. FIG. 8B illustrates a plot of the respective relative frequency shift as a function of temperature for mixtures of $^{87}$Rb either $N_2$ (diamonds), Kr (squares), or Ar (triangles). It may be seen that as the cell temperature increased, the relative frequency for the different mixtures shifted from about 8 to 16 MHz at about 25° C., to about 0 MHz at about 40° C., to about −10 to −22 MHz at about 57° C. Thus, it may be seen that absorption peaks of different substances vary with temperature, and thus suitably may be used to measure the temperature of the substance using the systems and methods provided herein.

Alternative Embodiments

As described herein, the present systems and methods may be used to optically, and directly, measure the temperature of a substance. It should be understood that such systems and methods readily may be incorporated into previously known technologies, such as atomic clocks or alkali magnetometers, so as to provide enhanced temperature measurement and control. In particular, $^{87}$Rb gas cells are presently used in atomic clocks that fly on global positioning system (GPS) and advanced extremely high frequency (AEHF) satellites. The $^{87}$Rb-based atomic clocks flying on these satellites currently use a contact-type temperature sensor, which measures the gas cell's temperature at one point, or a few points. Temperature perturbations external to the atomic clock are known to cause the actual alkali vapor's temperature to vary in a way that is not adequately compensated for by the control loop associated with the contact-type temperature sensor. Thus, it should be appreciated that using the present systems and methods to directly measure the temperature of the $^{87}$Rb in an atomic clock, the thermal control system of such clocks may be improved, and random-walk noise in such atomic clocks potentially may be greatly reduced. For example, an atomic clock or alkali magnetometer based on first transmission cell 32 suitably may be modified so as to include second transmission cell 52, a suitable laser beam transmitting therethrough (which may be from a second laser or may be a portion of the laser beam used to lock to first transmission cell 32), controller circuitry, and measurement circuitry such as described in greater detail above.

Additionally, while preferred embodiments of the invention are described herein, it will be apparent to one skilled in the art that various changes and modifications may be made. For example, although the above systems and methods primarily have been described with reference to measuring selected physical parameters of a substance, such as its temperature, density, its phase, pressure, or exposure to an electric or magnetic field, it should be understood that any physical parameter that causes a change in a feature of the absorption spectrum of the substance suitably may be measured. The appended claims are intended to cover all such changes and modifications that fall within the true spirit and scope of the invention.

What is claimed:

1. A system for measuring a physical parameter of a first substance having a first absorption spectrum with an absorption feature that varies based on the physical parameter, the system comprising:
    a second substance having a second absorption spectrum including first and second peaks respectively corresponding to first and second transitions of the second substance, the first and second peaks overlapping with one another, a point in the overlap between the first and second peaks defining an isoclinic point of the absorption spectrum of the second substance;
    at least one tunable-frequency laser configured to transmit a first laser beam through the first substance and to transmit a second laser beam through the second substance;
    a first photodetector configured to generate a first output based on an intensity of the first laser beam transmitted through the first substance;
    a second photodetector configured to generate a second output based on an intensity of the second laser beam transmitted through the second substance;
    controller circuitry configured to tune the at least one tunable-frequency laser so as to lock a first frequency of the first laser beam to the absorption feature of the first substance based on the first output, and to tune the at least one tunable-frequency laser so as to lock a second frequency of the second laser beam to the isoclinic point of the second substance based on the second output; and
    measurement circuitry configured to calculate the physical parameter of the first substance based on a difference between the first and second frequencies.

2. The system of claim 1, wherein the at least one tunable-frequency laser comprises a first tunable-frequency laser configured to generate the first laser beam and a second tunable-frequency laser configured to generate the second laser beam.

3. The system of claim 2, wherein the controller circuitry comprises:
    a first lock-in amplifier configured to receive the first output and to generate a first error signal based on the first output;
    a first controller in operable communication with the first tunable-frequency laser and the first lock-in amplifier, the first controller configured to tune the first frequency of the first tunable-frequency laser so as to minimize the first error signal and thus lock the first frequency to the temperature-dependent absorption feature of the first substance;
    a second lock-in amplifier configured to receive the second output and to generate a second error signal based on the second output; and
    a second controller in operable communication with the second tunable-frequency laser and the second lock-in amplifier, the second controller configured to tune the second frequency of the second tunable-frequency laser so as to minimize the second error signal and thus lock the second frequency to the isoclinic point of the second substance.

4. The system of claim 3, further comprising an optical component configured to generate an optical heterodyne of the first and second laser beams, the optical heterodyne having a beat frequency based on the difference between the first and second frequencies, and
    wherein the measurement circuitry comprises a third photodetector configured to generate a third output based on the optical heterodyne, a frequency counter configured to determine the beat frequency based on the third output, and a calculation module configured to calculate the physical parameter based on the determined beat frequency and a calibration constant.

5. The system of claim 4, wherein the optical component comprises a beamsplitter configured to receive a portion of each of the first and second laser beams and to direct the received portions to the third photodetector.

6. The system of claim 3, wherein the first and second controllers are respectively configured to tune the first and second tunable-frequency lasers by respectively adjusting driver currents of the first and second tunable-frequency lasers.

7. The system of claim 1, wherein the at least one tunable-frequency laser is configured to generate a frequency comb comprising the first frequency and the second frequency, the first and second frequencies being separated from one another by an integer multiple of a spacing of the frequency comb.

8. The system of claim 7, wherein the controller circuitry comprises:
a first lock-in amplifier configured to receive the first output and to generate a first error signal based on the first output;
a first controller in operable communication with the at least one tunable-frequency laser and the first lock-in amplifier, the first controller configured to tune the first frequency of the at least one tunable-frequency laser so as to minimize the first error signal and thus lock the first frequency to the temperature-dependent absorption feature of the first substance;
a second lock-in amplifier configured to receive the second output and to generate a second error signal based on the second output; and
a second controller in operable communication with the at least one tunable-frequency laser and the second lock-in amplifier, the second controller configured to tune the spacing of the at least one tunable-frequency laser so as to minimize the second error signal and thus lock the second frequency to the isoclinic point of the second substance.

9. The system of claim 8, wherein the measurement circuitry is configured to determine the spacing of the at least one tunable-frequency laser based on a third output of the at least one tunable-frequency laser, to determine the difference between the first and second frequencies based on the determined spacing, and to calculate the physical parameter based on the determined difference and a calibration constant.

10. The system of claim 7, wherein the controller circuitry comprises:
a first lock-in amplifier configured to receive the first output and to generate a first error signal based on the first output;
a first controller in operable communication with the at least one tunable-frequency laser and the first lock-in amplifier, the first controller configured to tune the spacing of the at least one tunable-frequency laser so as to minimize the first error signal and thus lock the first frequency to the temperature-dependent absorption feature of the first substance;
a second lock-in amplifier configured to receive the second output and to generate a second error signal based on the second output; and
a second controller in operable communication with the at least one tunable-frequency laser and the second lock-in amplifier, the second controller configured to tune the second frequency of the at least one tunable-frequency laser so as to minimize the second error signal and thus lock the second frequency to the isoclinic point of the second substance.

11. The system of claim 1, wherein the second substance comprises an atomic gas, and wherein the first and second transitions are electronic transitions of atoms in the atomic gas.

12. The system of claim 11, wherein the atomic gas comprises an alkali selected from the group consisting of $^{87}$Rb, $^7$Li, $^{23}$Na, $^{39}$K, and $^{41}$K.

13. The system of claim 11, wherein the first substance comprises the atomic gas, and wherein the absorption feature corresponds to a third electronic transition of the atomic gas.

14. The system of claim 13, wherein the first substance further comprises a buffer gas.

15. The system of claim 1, wherein the absorption feature of the first substance corresponds to an atomic electronic transition, a molecular electronic transition, a vibrational transition, a rotational transition, or a rovibrational transition.

16. The system of claim 1, wherein the physical parameter comprises temperature, pressure, density, phase, or exposure to an electric or magnetic field.

17. The system of claim 1, further comprising adjustment circuitry configured to adjust the physical parameter of the first substance based on the determined physical parameter.

18. A method for measuring a physical parameter of a first substance having a first absorption spectrum with an absorption feature that varies based on the physical parameter, the method comprising:
transmitting a first laser beam through the first substance;
transmitting a second laser beam through a second substance having an absorption spectrum including first and second peaks respectively corresponding to first and second transitions of the second substance, the first and second peaks overlapping with one another, a point in the overlap between the first and second peaks defining an isoclinic point of the absorption spectrum of the second gas;
generating a first output based on an intensity of the first laser beam transmitted through the first substance;
generating a second output based on an intensity of the second laser beam transmitted through the second substance;
locking a first frequency of the first laser beam to the absorption feature of the first substance based on the first output;
locking a second frequency of the second laser beam to the isoclinic point of the second substance based on the second output; and
calculating the physical parameter of the first substance based on a difference between the first and second frequencies.

19. The method of claim 18, comprising generating the first laser beam with a first tunable-frequency laser, and generating the second laser beam with a second tunable-frequency laser.

20. The method of claim 19, wherein locking the first frequency to the absorption feature of the first substance based on the first output comprises:
at a first lock-in amplifier, receiving the first output and generating a first error signal based on the first output;
at a first controller in operable communication with the first tunable-frequency laser and the first lock-in amplifier, tuning the first tunable-frequency laser so as to minimize the first error signal and thus lock the first frequency to the absorption feature of the first substance; and
wherein locking the second frequency to the isoclinic point of the second substance based on the second output comprises:
at a second lock-in amplifier, receiving the second output and generating a second error signal based on the second output; and
at a second controller in operable communication with the second tunable-frequency laser and the second lock-in amplifier, tuning the second tunable-frequency laser so as to minimize the second error signal and thus lock the second frequency to the isoclinic point of the second substance.

21. The method of claim 20, further comprising generating an optical heterodyne of the first and second laser beams, the optical heterodyne having a beat frequency based on the difference between the first and second frequencies;
  generating a third output based on the optical heterodyne;
  determining the beat frequency based on the third output; and
  calculating the physical parameter of the first substance based on the determined beat frequency and a calibration constant.

22. The method of claim 21, wherein generating said optical heterodyne comprises receiving a portion of each of the first and second laser beams at a beamsplitter and directing the received portions to a third photodetector configured to generate the third output.

23. The method of claim 20, wherein the first and second controllers respectively tune the first and second tunable-frequency lasers by respectively adjusting driver currents of the first and second tunable-frequency lasers.

24. The method of claim 18, comprising generating a frequency comb at the at least one tunable-frequency laser, the frequency comb comprising the first frequency and the second frequency, the first and second frequencies being separated from one another by an integer multiple of a spacing of the frequency comb.

25. The method of claim 24, wherein locking the first frequency to the absorption feature of the first substance based on the first output comprises:
  at a first lock-in amplifier, receiving the first output and generating a first error signal based on the first output;
  at a first controller in operable communication with the at least one tunable-frequency laser and the first lock-in amplifier, tuning the first frequency of the at least one tunable-frequency laser so as to minimize the first error signal and thus lock the first frequency to the absorption feature of the first substance; and
  wherein locking the second frequency to the isoclinic point of the second substance based on the second output comprises:
    at a second lock-in amplifier, receiving the second output and generating a second error signal based on the second output; and
    at a second controller in operable communication with the second tunable-frequency laser and the second lock-in amplifier, tuning the spacing of the at least one tunable-frequency laser so as to minimize the second error signal and thus lock the second frequency to the isoclinic point of the second substance.

26. The method of claim 25, comprising determining the spacing of the at least one tunable-frequency laser based on a third output of the at least one tunable-frequency laser, determining the difference between the first and second frequencies based on the determined spacing, and calculating the physical parameter based on the determined difference and a calibration constant.

27. The method of claim 24, wherein locking the first frequency to the absorption feature of the first substance based on the first output comprises:
  at a first lock-in amplifier, receiving the first output and generating a first error signal based on the first output;
  at a first controller in operable communication with the at least one tunable-frequency laser and the first lock-in amplifier, tuning the spacing of the at least one tunable-frequency laser so as to minimize the first error signal and thus lock the first frequency to the absorption feature of the first substance; and
  wherein locking the second frequency to the isoclinic point of the second substance based on the second output comprises:
    at a second lock-in amplifier, receiving the second output and generating a second error signal based on the second output; and
    at a second controller in operable communication with the second tunable-frequency laser and the second lock-in amplifier, tuning the second frequency of the at least one tunable-frequency laser so as to minimize the second error signal and thus lock the second frequency to the isoclinic point of the second substance.

28. The method of claim 18, wherein the second substance comprises an atomic gas, and wherein the first and second transitions are electronic transitions of atoms in the atomic gas.

29. The method of claim 28, wherein the atomic gas comprises an alkali selected from the group consisting of $^{87}$Rb, $^{7}$Li, $^{23}$Na, $^{39}$K, and $^{41}$K.

30. The method of claim 28, wherein the first substance comprises the atomic gas, and wherein the absorption feature corresponds to a third electronic transition of the atomic gas.

31. The method of claim 30, wherein the first substance further comprises a buffer gas.

32. The method of claim 18, wherein the absorption feature of the first substance corresponds to an atomic electronic transition, a molecular electronic transition, a vibrational transition, a rotational transition, or a rovibrational transition.

33. The method of claim 18, wherein the physical parameter comprises temperature, pressure, density, phase, or exposure to an electric or magnetic field.

34. The method of claim 18, further comprising adjusting the physical parameter of the first substance based on the determined physical parameter.

* * * * *